United States Patent
Prusky et al.

(10) Patent No.: US 11,583,178 B2
(45) Date of Patent: Feb. 21, 2023

(54) SYSTEMS AND METHODS FOR EVALUATING CONTRAST SENSITIVITY AND OTHER VISUAL METRICS

(71) Applicant: Burke Neurological Institute, White Plains, NY (US)

(72) Inventors: Glen Prusky, White Plains, NY (US); Scott William Joseph Mooney, New York, NY (US); Nicholas Jeremy Hill, White Plains, NY (US)

(73) Assignee: Burke Neurological Institute, White Plains, NY (US)

( * ) Notice: Subject to any disclaimer, the term of this patent is extended or adjusted under 35 U.S.C. 154(b) by 580 days.

(21) Appl. No.: 16/661,596

(22) Filed: Oct. 23, 2019

(65) Prior Publication Data

US 2020/0121179 A1 Apr. 23, 2020

Related U.S. Application Data

(60) Provisional application No. 62/749,360, filed on Oct. 23, 2018.

(51) Int. Cl.
*A61B 3/02* (2006.01)
*A61B 3/00* (2006.01)
*A61B 3/113* (2006.01)

(52) U.S. Cl.
CPC .......... *A61B 3/022* (2013.01); *A61B 3/0091* (2013.01); *A61B 3/113* (2013.01)

(58) Field of Classification Search
CPC ........ A61B 3/022; A61B 3/0091; A61B 3/113
USPC .......................................................... 600/558
See application file for complete search history.

(56) References Cited

U.S. PATENT DOCUMENTS

| | | | |
|---|---|---|---|
| 11,122,999 B2 | 9/2021 | Hill et al. | |
| 2007/0182929 A1* | 8/2007 | Feher | A61B 3/063 351/243 |
| 2009/0153796 A1* | 6/2009 | Rabner | A61B 3/024 351/203 |
| 2016/0262608 A1 | 9/2016 | Krueger | |
| 2016/0271002 A9 | 9/2016 | Simmons | |
| 2017/0007111 A1* | 1/2017 | Samec | A61B 5/369 |
| 2017/0007122 A1 | 1/2017 | Samec et al. | |

FOREIGN PATENT DOCUMENTS

WO 2018006013 A1 1/2018

OTHER PUBLICATIONS

International Search Report and Written Opinion issued for PCT/US2019/057638, dated Feb. 18, 2020.
Extended European Search Report dated Jun. 15, 2022 issued in European Patent Application No. 19877442.4.
Metzger et al., "Haptic Saliency Model for Rigid Textured Surfaces," Advances in Biometrics: International Conference ICB 2007, Seoul, Korea, Aug. 27-29, 2007, (Lecture Notes in Computer Science), Springer Intl. Publishing AG, part of Springer Nature 2018, EuroHaptics 2018, Bedin, Heidelberg, Germany, pp. 389-400.

(Continued)

*Primary Examiner* — Mohammed A Hasan
(74) *Attorney, Agent, or Firm* — Amster, Rothstein & Ebenstein LLP

(57) ABSTRACT

Methods, systems and devices for determining contrast sensitivity function in a subject without requiring perceptual report by the subject.

27 Claims, 20 Drawing Sheets

(56) References Cited

OTHER PUBLICATIONS

Weier et al., "Foveated Real-Time Ray Tracing for Head-Mounted Displays," Pacific Graphics 2016, vol. 35, No. 7, Oct. 27, 2016, Computer Graphics Forum: Journal of the European Association for Computer Graphics, Wiley-Blackwell, Oxford, pp. 289-298.
Burr et al., "Saccadic Suppression Precedes Visual Motion Analysis," Brief Communication, Current Biology, vol. 9, No. 20, Oct. 11, 1999, pp. 1207-1209.

\* cited by examiner

FIGURE 2A
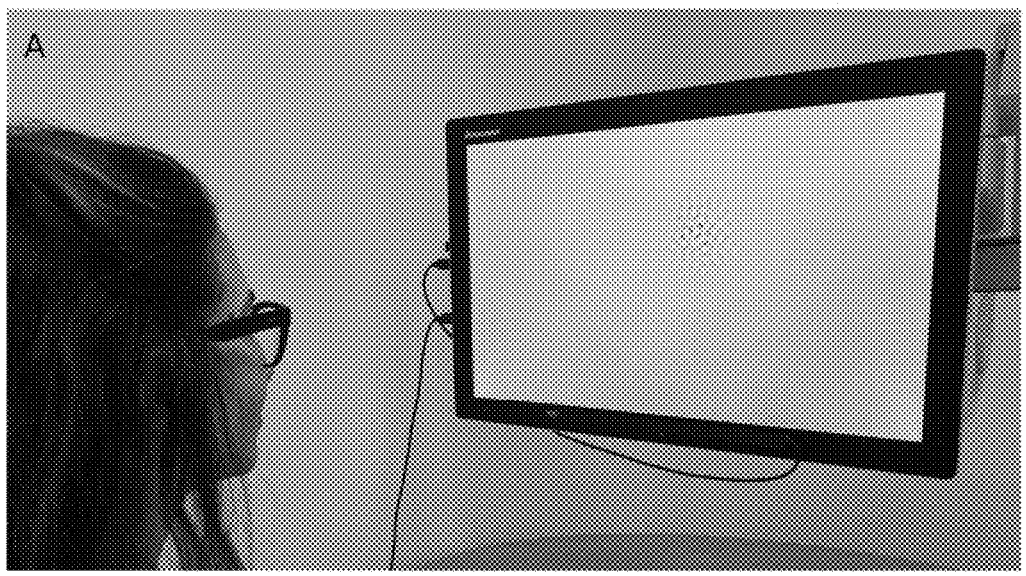
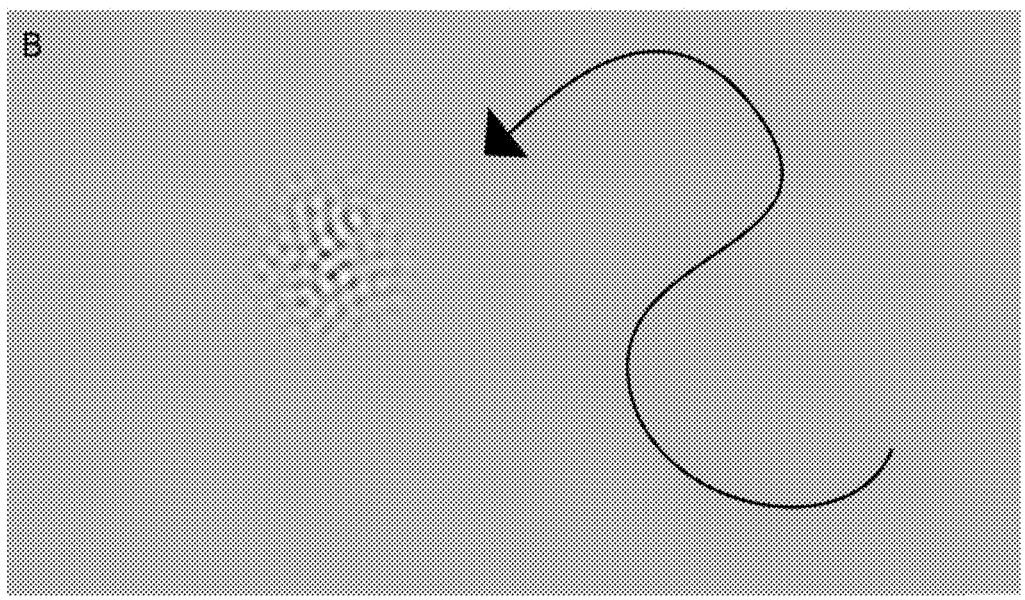
FIGURE 2B

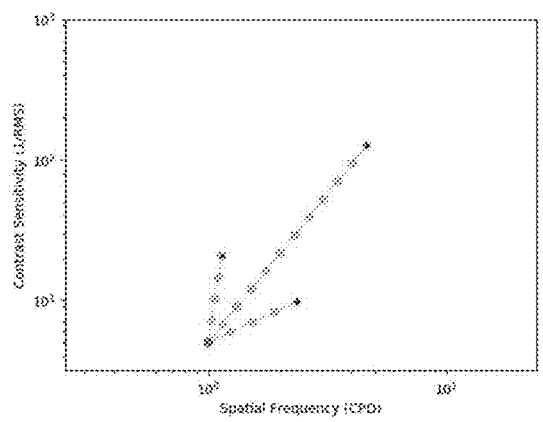 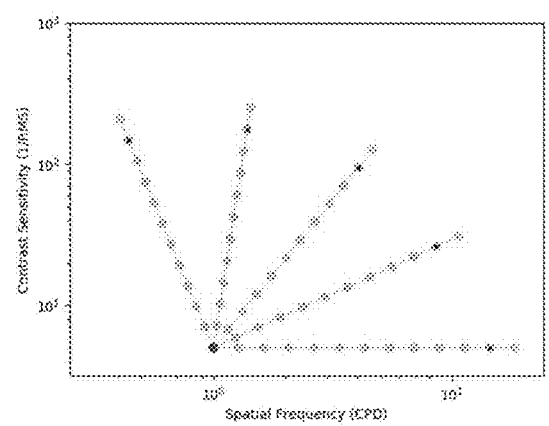
FIGURE 11A                    FIGURE 11B

SYSTEMS AND METHODS FOR EVALUATING CONTRAST SENSITIVITY AND OTHER VISUAL METRICS

CROSS-REFERENCE TO RELATED APPLICATIONS

This application claims the benefit of U.S. Provisional Patent Application No. 62/749,360, filed on Oct. 23, 2018. The entire contents of that application are incorporated herein by reference.

STATEMENT OF GOVERNMENT SUPPORT

This invention was made with government support under grant numbers EY030156 and EY026753 awarded by the National Institutes of Health. The government has certain rights in the invention.

FIELD OF THE INVENTION

This invention relates to the field of assessing visual perception, and specifically to systems and methods for (a) inferring the visibility of visual stimuli from eye tracker data and (b) assessing the contrast sensitivity function.

BACKGROUND OF THE INVENTION

The contrast sensitivity function (CSF) is a useful measure of visual system performance because it quantifies fundamental features of how the visual system extracts form from light, and is well correlated with many other measures of visual health and disease. The best means through which to assess the CSF, however, is a matter of ongoing research. Unlike other measures of basic visual function, the CSF describes a continuum of sensitivity thresholds and is consequently more difficult to assess than one-dimensional measures such as visual acuity. It can be constructed from a sequence of independent contrast thresholds computed at different spatial frequencies, but the time required to measure multiple thresholds with conventional psychophysical staircase procedures is unrealistic in clinical settings. Newer variants of the staircase technique reduce the time required to estimate the CSF by using adaptive Bayesian algorithms to repeatedly compute the most informative combination of spatial frequency and contrast to present in each trial. These methods often directly model the CSF as a parameterized function rather than fitting a curve to independent thresholds obtained at different spatial frequencies.

Simultaneous two-dimensional Bayesian approaches can estimate a participant's CSF in less than five minutes and can even be run on a portable device, but they do not address one of the fundamental restrictions of traditional psychophysical tasks: their reliance on extended periods of attention and volitional perceptual report. The tasks can be tedious because they require the repeated presentation of visually uninteresting stimuli such as filtered noise patterns and sinusoidal gratings. Adaptive procedures also naturally become more difficult as the threshold of an observer's ability is approached; by design, these tasks spend as much time as possible presenting stimuli at peri-threshold combinations of contrast and spatial frequency. These procedures can be tolerated by healthy adults, particularly if they are offered incentives, but are not well tolerated by observers who are less willing or less able to engage with the test, such as children or individuals with brain injury.

The only available workaround for less motivated subjects has been to add more trials (and hence more time) to the task. This strategy, however, does not help individuals (of any age) who have difficulty sustaining attention, following task instructions, or communicating their responses to an experimenter. There are alternatives to report-based tasks for these populations, but they also have significant shortcomings that have prevented them from being routinely used in clinical settings. Preferential looking paradigms such as Teller cards circumvent the need for verbal communication, but they are still highly dependent on the participant's attention span. Electrophysiological measures such as visual evoked potentials are also constrained by attention, and require specialized training to administer, can be unpleasant for the participant, and have reduced sensitivity relative to behavioral report.

Previous studies have assessed contrast sensitivity in rodents by filling their visual field with drifting gratings and observing which combinations of spatial frequency and contrast elicit the optokinetic nystagmus (OKN) response, which is a reflex that induces smooth conjugate eye movements to stabilize the visual world on the retina. A similar technique has been used to measure contrast sensitivity in humans (Dakin, S. C., & Turnbull, P. R (2016). Similar Contrast Sensitivity Functions Measured Using Psychophysics and Optokinetic Nystagmus, Scientific Reports, 6, 34514). An eye tracker was used to detect the direction of OKN in response to full-screen drifting noise on a computer display and found that trial outcomes classified by OKN direction produced sensitivity thresholds that were similar to thresholds obtained from perceptual report. This approach takes promising steps toward contrast sensitivity assessment in non-communicative populations: the task does not rely on volitional report and can potentially be administered without instruction provided that the participant attends to the screen. Other elements of this procedure, however, are likely to pose problems for many participants. The procedure takes almost twenty minutes to complete, which is an unrealistic requirement for inattentive or cognitively impaired participants. The time can be reduced by combining the procedure with an adaptive staircase, but it is unclear how well this would work, as their OKN matching algorithm has a false positive rate of 50% and the time-sensitive nature of the task's individual trials appear vulnerable to lapses in attention.

SUMMARY OF THE INVENTION

The present invention discloses novel systems and methods for rapidly estimating the contrast sensitivity function (CSF) using eye movements. The present invention, referred to herein as "Curveball", minimizes the influences of attention, motivation, and communicative ability on task performance without sacrificing the efficiency of conventional methods. The present invention may comprise five distinct steps as shown in FIG. 1 and described below. Numerous variations and combinations of these steps may be utilized in the preferred embodiment, including but not limited to the complete omission of one or more steps. Additional components of the invention are also described below.

Where the present disclosure refers to "gaze", "gaze data", "gaze samples", "gaze position", and other descriptions of data generated by the eye tracker hardware, the gaze data referred to may be one or both monocular streams of data (i.e. data that describes the 2D gaze position on the display and the 3D absolute position in space of a single eye) or a combined binocular stream computed from both monocular streams. In ideal circumstances, monocular data streams may be used, and each aspect of gaze data processing described below (e.g. saccade detection, blink detection) may be performed separately for each available monocular stream or may combine data from both monocular streams. The user may also elect to measure only one monocular stream by obscuring one of the subject's eyes or by manipulating the eye tracker hardware and/or data processing algorithms. The availability of monocular streams may depend on the available eye tracker hardware in different embodiments of the invention; where only a single binocular stream is available, the gaze data processing described below may be performed for that stream. In this case, binocular variants of the processing algorithms may be used.

At the Stimulus Generation Step (110), one or more "stimulus sweeps" may be created. A stimulus sweep may comprise an ordered sequence of one or more visual stimuli. Each stimulus may be parameterized by a spatial frequency value and a contrast value. The stimuli may be sine wave gratings, band-filtered isotropic or anisotropic image textures (e.g. randomly generated noise), or a combination of both. If band-filtered textures are used, they may be produced by taking 1/f amplitude spectrum noise with a random phase spectrum and multiplied in the frequency domain with an annular band-pass filter centered on the target spatial frequency that has a width of 10% of the target spatial frequency. The sequences of spatial frequency and contrast configurations that make up each sweep may form a continuous trajectory through the CSF space (e.g. a straight or curved line) or may be arbitrary (e.g. a random sequence of parameter pairs).

The sequences may be predetermined in advance of the Presentation/Response Step (140) (described further below) or defined "on the fly" during the Presentation/Response Step (140) in response to participant input. Similarly, the stimulus textures may be generated in advance of the Presentation/Response Step (140) or created "on the fly" during the Presentation/Response Step (140). The stimuli may be windowed with a continuous function that reduces contrast as a function of radial distance from the center of the stimulus (e.g. a Hann window). The stimulus size may vary depending on the spatial frequency of the stimulus texture, the number of sweeps that will be presented simultaneously, the size of the physical display, and the measurement needs of the particular test being performed.

The stimuli may be filtered using an anisotropic bandpass filter to ensure that temporal aliasing does not occur during stimulus motion. For example, the filter may remove all components with horizontal spatial frequency greater than 2.85 cycles per degree (CPD), which is 95% of the Nyquist limit (3 CPD) of a stimulus moving at 10 degrees per second on a display with a refresh rate of 60 Hz. Different anisotropic filters may be applied at different stimulus speeds as the Nyquist limit changes. The orientation of the noise patch may be continuously steered into its direction of motion to keep the anti-aliased direction of this filter "facing forward" at all times.

At the Gaze Pre-Calibration Step (120), a set of predetermined stimuli are presented on a uniform background on the display to calibrate the eye tracker. These stimuli may be small shapes (e.g. a disc with holes cut out of it) and their quantity and arrangement may depend on the mode of calibration desired for that particular participant and data collection session. The background may be, for example, black, or any other uniform color or shade.

In one-point calibration mode, a single stimulus is presented. The stimulus may be presented in the center of the display, or in another location on the display. For each updated display frame in which the participant's gaze falls within a certain radius of the stimulus (for example, 5 degrees of visual arc), the participant is presumed to be fixating upon the stimulus, and the difference vector between the gaze position and true stimulus position may be used to update a calibration translation vector. The final calibration vector may be used throughout the remainder of the steps to correct all gaze position data reported by the eye tracker for that participant.

In four-point calibration mode, four stimuli are presented instead, for example, one in each corner of the screen. A calibration translation vector may be updated independently for each corner's stimulus using the same method as the one-point calibration mode. The resulting four calibration vectors may be used to create an interpolated perspective mapping that may be used to correct all future gaze position data. The Gaze Pre-Calibration Step (120) may be omitted if calibration is unfeasible for the participant or if the existing calibration of the eye tracker is sufficient.

At the Stimulus Pathing Step (130), a determination may be made as to how the sine wave grating or band-filtered texture stimuli will move during the Presentation/Response Step (140). The stimuli may follow one or more predetermined paths that have been programmed and stored in memory in advance, or their paths may be procedurally generated by an algorithm. For example, the stimuli may move within an invisible grid, may avoid collisions with other stimuli by not moving to grid cells that are currently occupied, and may avoid repeating the same type of movement twice in a row and/or making the same type of concurrent movement as other active stimuli. The procedural generation may determine stimulus paths in advance of the Presentation/Response Step (140) and/or generate upcoming path segments "on the fly" during that step. The initial positions of the stimuli may be predetermined or random, with or without additional restrictions (e.g. preventing multiple stimuli from appearing at the same location).

Stimulus speed may change throughout the path and/or vary both between and within method applications as a function of participant responses or to facilitate different measurement needs or display devices. For example, stimuli may move at 10 degrees per second on a larger display when following a straight path, but decrease in speed to 8 degrees per second when following a curved path.

The Presentation/Response Step (140) comprises the core loop of the invention. One or more stimulus sweeps are selected to be presented to the participant. One or more stimulus sweeps may be presented simultaneously. At the beginning of the procedure, the first stimulus in each of these selected sweeps may be presented, or a number of stimuli at the beginning of the sweep sequence may be skipped (for example, if progress on that sweep has already been made in a previous session with that participant). While visible, the stimuli may move along one or more paths generated in advance of the Presentation/Response Step (140) and/or may move along a path determined "on the fly" during the Presentation/Response Step (140).

Each sweep has an "evidence-of-visibility" score, which indicates the current strength of evidence that the participant can see the currently active stimulus in that sweep. While a sweep is active during the Presentation/Response Step (140) (i.e. its current stimulus is displayed), this evidence-of-visibility score is monitored and updated. The evidence-of-visibility scores are used to determine when the current stimulus should be modified or exchanged for the next stimulus in that sweep, to calibrate the participant's gaze data, and to calculate the participant's visual function.

The Presentation/Response Step (140) also uses a "global evidence" score, which is continuously monitored and updated. This score indicates whether the current stimuli of any active sweeps are visible to the participant, and informs the stopping criterion for the Presentation/Response Step (140). If only one sweep is active, the global evidence score may simply be the evidence-of-visibility score of that sweep. If more than one sweep is active, the global evidence score may be computed from the combination of evidence-of-visibility scores of one or more active sweeps, or it may be computed independently of any sweeps (e.g. by determining if the participant is looking away from the display).

An algorithm continuously (e.g. at the same rate as the display refresh rate) monitors the participant's gaze response to all active stimuli and, in response to specific patterns of gaze input and stimulus attributes, may (a) update the evidence-of-visibility score of any active sweep, (b) update the global evidence score, and/or (c) start or stop presenting a novel audiovisual stimulus to provide feedback to the participant.

The patterns of gaze input that trigger these continuous responses may include fixations, saccades, smooth pursuits, target tracking, optokinetic nystagmus, and/or blinks. The algorithm that classifies these gaze responses may also detect "impossible" eye movements that suggest that the eye tracker is unable to obtain a reliable estimate of the participant's gaze, and alert the Curveball user accordingly. When the algorithm detects that the participant is not in front of the display, or detects that the participant's distance is too close to or too far away from the display, the task may be paused automatically until the participant is in front of the display within a permitted distance range (e.g. 400 to 800 millimeters).

The algorithms used to detect and classify different types of gaze responses may vary; some example algorithms are described below. Different algorithms, for example, may be required for different eye tracking hardware used in different embodiments of the invention. The statistics employed by these algorithms may be computed continuously while practicing the present invention and used for analytic and feedback purposes other than the exemplary classifications described herein.

Fixation events may be detected by analyzing the two-dimensional dispersion metric of the x/y gaze coordinates over a sliding time window of gaze samples (e.g. 0.15 seconds) each time a new gaze sample arrives. Gaze samples may be classified as part of an ongoing fixation event when the mean dispersion over this time window falls below a certain threshold. The mean position of the fixation event may be compared to the position of one or more active stimuli to determine which of those stimuli may be fixated ("target fixation").

Saccade events may be detected by analyzing gaze velocity over a sliding time window of gaze samples (e.g. 0.15 seconds) each time a new gaze sample arrives. Saccades may start when the magnitude of this velocity rises above a certain "start" threshold (e.g. 50 degrees per second) and persist through future gaze samples as long as the magnitude remains above a certain "end" threshold, which may differ from the start threshold (e.g. 30 degrees per second). False positives of this algorithm may be detected by additionally restricting the change in velocity direction from sample to sample below a certain angle (e.g. 90 degrees) after a saccade has started and/or ignoring detected saccades with a duration below a certain threshold (e.g. 50 milliseconds).

Smooth pursuit events may be detected by analyzing gaze velocity and acceleration over a sliding time window of gaze samples (e.g. 0.15 seconds) each time a new gaze sample arrives. Smooth pursuits may start when the magnitude of gaze velocity falls between certain minimum and maximum "start" thresholds (e.g. 5 degrees per second to 20 degrees per second) and the rate of change in the direction of gaze velocity is less than a certain angular value (e.g. 180 degrees per second), and persists as long as gaze velocity continues to fall within these thresholds.

Target tracking events may be detected by analyzing gaze position over a sliding time window of gaze samples (e.g. 0.15 seconds) each time a new gaze sample arrives, and comparing it to the position of a given target over the same time window. The algorithm may report that the participant is tracking that target if a sufficient proportion of gaze samples within that time window (e.g. at least 90%) fall within a certain distance of the position of the target at the same moment (e.g. 0.4 degrees of visual arc). The coordinates of the target to which gaze position is compared may be its absolute position on the display, or may first be corrected by subtracting the current gaze position from each target position sample so that any systematic offset between the target trajectory and gaze trajectory is ignored (e.g. the participant may not be tracking the exact center of the target). Target tracking may need to persist for some number of contiguous samples (e.g. five samples) before it is confirmed as a true positive classification.

Optokinetic nystagmus events may be detected in a similar way to target tracking, but the trajectory of the participant's gaze may be required to be linear and interspersed with saccades whose velocity is in the opposite direction to the trajectory.

Blinks may be detected using an algorithm that varies with the exact eye tracker hardware used during the application of the method, as different eye trackers may produce different "signature" responses to blinks. For example, blinks may be classified by detecting periods in which no gaze data is reported by the eye tracker for no longer than a predetermined time (e.g. two seconds). Gaze samples immediately before and/or immediately after the detected blink (e.g. up to 0.5 seconds on each side) may be ignored to avoid the risk of using malformed gaze data during the blink.

The evidence-of-visibility score may be assigned a starting value prior to the Presentation/Response Step (140). The starting value may be zero, 100, or another value. During the Presentation/Response Step (140), different gaze responses may then affect the evidence-of-visibility score of one or more sweeps and/or the global evidence score in different ways. For example, responses that indicate that an active sweep stimulus is visible to the participant, such as fixations that match the position of a stimulus, saccades that start from another point on the display and end at the position of a stimulus, and persistent tracking of a stimulus as it moves, may add certain predetermined values to the evidence-of-visibility score for that stimulus's sweep. The value added may represent the weight of that response's evidence (e.g. 1 point per frame of target fixation, 5 points per saccade-to-target, and 10 points per frame of target tracking). Responses that indicate that an active sweep stimulus is not visible to the participant, such as "searching" saccade behavior (which may be classified as a series of repeated saccades to non-target positions in opposing directions) or looking away from the screen, may subtract certain predetermined values from the evidence-of-visibility score for all sweeps and/or the global evidence score (e.g. 5 points per searching saccade, 1 point per frame of looking off-screen). Evidenceof-visibility and/or global evidence scores may decrease by a certain value automatically per frame (e.g. 1 point).

The value of evidence from target tracking may be weighted by a continuous auto-correlation analysis of the target trajectory, e.g. so that tracking targets that follow less predictable trajectories (e.g. more curved, more frequency and more abrupt turns) adds less evidence-of-visibility to that target stimulus's sweep. The tracking evidence value, for example, may be multiplied by 1 minus the auto-correlation coefficient of the stimulus over a sliding time window of a certain duration (e.g. 1 second).

The system may determine whether a sweep's evidence-of-visibility score exceeds or falls below a certain threshold, or falls within or outside a certain range. The exact evidence threshold or range may vary both between and within method applications as a function of the parameters of the active stimulus in that sweep or to facilitate different measurement needs.

Whenever a sweep's evidence-of-visibility score exceeds a certain threshold or falls within a certain range, it may be inferred that the participant can see the active stimulus in that sweep, and the stimulus may have its appearance altered (for example, an increase or decrease in contrast, size, or speed), or may be swapped out entirely for the next stimulus in that sweep's sequence, at which point that sweep's evidence-of-visibility score is reset to the starting value. Whenever a sweep's evidence-of-visibility score falls below a certain threshold or falls outside a certain range, it may be inferred that the participant cannot see the active stimulus in that sweep, and the system may terminate display of the visual stimulus, and present on the display a visual stimulus of another sequence of visual stimuli. The sweep's evidence-of-visibility score would begin at the starting value. Prior to the Presentation/Response Step (140), an algorithm may be used to determine paths each visual stimulus will follow.

When the global evidence score falls below a certain threshold, it may be inferred that none of the currently active stimuli in the currently presented sweeps are visible to the participant, and the trial may be terminated. All evidence-of-visibility scores and stimulus changes that occurred within each sweep may be recorded to inform the CSF Analysis Step (150) and/or to skip some number of stimuli in future presentations of the same sweep. A new trial may then begin with new sweeps and/or repeated presentations of previous sweeps, possibly following an intermission phase where other stimuli are presented to provide a break and/or reward for the participant. If the method infers that sufficient data has been collected (e.g. a predetermined number of trials has been completed for each sweep), the Presentation/Response Step (140) may end.

A sweep's evidence-of-visibility score may also be used to continuously calibrate the eye tracker in real time as the current stimulus of that sweep and/or the participant's gaze move to different areas of the display. The eye tracker hardware used in a given embodiment of the invention may not be able to accurately calibrate a participant's gaze to the screen used in that embodiment, in which case the one-off calibration performed in the Gaze Pre-Calibration Step (120) may not be suitable for the entirety of the display. When a stimulus's evidence-of-visibility score is sufficiently high during the Presentation/Response Step (140) and the participant is determined to be fixating on a stimulus, the calibration parameters may be adjusted to improve the accuracy of gaze position data in the region of the display currently occupied by the stimulus. This improvement may change the parameters of a one-point calibration or a four-point calibration. In this way, evidence-of-visibility scores may be used as feedback to improve future computations of evidence-of-visibility scores.

Other types of data provided by the eye tracker hardware may also be used in the gaze processing algorithms of the invention's software. Eye distance, for example, may be used to monitor and act upon the participant's distance from the display and determine the true spatial frequency (in degrees of visual arc, relative to the participant's true distance from the display) of any stimuli being presented. Head pose data, where provided, may be used to continuously determine which of the participant's eyes are currently visible to the eye tracker and whether the participant is facing the display.

Additional images, animations, and/or videos may be presented in tandem with the stimuli or between trials to facilitate task attention or provide a reward or break to the participant. The images may be, for example, semi-transparent textures superimposed on the moving noise target to quickly draw a participant's attention to the noise target. For example, a cartoon ghost may appear on top of the stimulus at the start of each trial to draw the observer's gaze, and then disappears upon initial fixation. The assistive image may fade out as soon as the participant's gaze comes within, for example, 5 degrees of the image.

As a further example, one or more images or animations (e.g. animated fireworks) may, for example, appear as a visual reward for a predetermined amount of time (e.g. two seconds) at the end of a trial or when a certain duration or quality of gaze response is detected. As a further example, a video may be played on the computer screen between trials to provide the participant with temporary relief from the task. These images, animations, and videos may or may not include audio content.

At the Contrast Sensitivity Function (CSF) Analysis Step (150), the progress made on all sweeps in all completed trials is used to compute an estimate of part or all of the participant's CSF. The final configurations of spatial frequency and contrast that were presented for each sweep (the "sweep thresholds") may be interpreted as estimates of the boundary of the CSF, which separates visible combinations of spatial frequency and contrast from invisible combinations. A polynomial or other non-linear function may be fitted to these sweep thresholds to compute an interpolated estimate of the entire curve, or individual sweep thresholds may be used as individual measures of the CSF. For example, a sweep comprising stimuli of increasing spatial frequency and constant contrast may be interpreted as an estimate of the participant's high-contrast or low-contrast acuity. Alternatively, as another example, a sweep comprising stimuli of constant spatial frequency of 1 cycle per degree of visual arc and decreasing contrast may be interpreted as an estimate of the participant's peak contrast sensitivity.

Another component of the present invention includes an algorithm to analyze a data set of CSFs to determine the subset of one or more measured sweeps (the "basis sweeps") whose thresholds are, statistically, the most highly predictive of the CSF computed from the full set of sweeps in the same population. The predictive value of a subset of sweeps may be computed using a multivariate multiple regression with the full set of sweeps as the dependent variables. This algorithm may be used to reduce the number of sweeps required to robustly estimate the CSF in future Curveball sessions within that population. The single sweep whose threshold is most predictive of the entire CSF of a participant from that population is labeled as the "Concuity" sweep of that population. The empirical identification of the Concuity sweep is a novel feature of the present invention.

Variations of the present invention may be used to assess visual functions other than the contrast sensitivity function. The visual stimuli comprising the sweep sequences may be parameterized along dimensions other than spatial frequency and contrast, and may be generated in visual forms other than sine wave gratings or band-filtered noise textures. The Gaze Pre-Calibration Step (120), Stimulus Pathing Step (130), and Presentation/Response Step (140) may be otherwise identical for these varied applications. The evidence-of-visibility scores may be used to calculate visual functions relevant to the dimensions of any stimulus parameterization, by finding the threshold between stimulus visibility and stimulus invisibility along the dimensions that vary across the sweep sequence. Examples of such dimensions include, without limitation: stimulus orientation; stimulus color contrast; the speed and/or direction of stimulus motion; stimulus size; stimulus temporal frequency; and stimulus position relative to fixation. Any such stimulus dimensions can be combined in a given application of the present invention, and the methods of the invention can be used to estimate and describe the N-dimensional psychophysical threshold manifold separating combinations of stimulus parameters that are visible to the participant from combinations of parameters that produce invisible stimuli. Data sets of such thresholds measured in populations may then be used to statistically determine the subset of sweeps that are most predictive of those thresholds, in the same way as described above for contrast sensitivity.

Another aspect of the present invention is the physical hardware on which the above procedure is installed and run as software. Various configurations of displays, computers, and eye tracker components may be used to practice the present invention. For example, the invention may be practiced with an all-in-one computer, which may be attached to a mobile apparatus that allows the display to be positioned in front of an immobile participant at an appropriate distance, or stabilized in some other fashion (e.g. simply positioned on a flat surface). Alternatively, the present invention may be practiced using a device such as a tablet, a laptop, a mobile phone, a virtual-reality or augmented-reality display device, or a monitor attached to a desktop computer. The eye tracker used to measure the participant's gaze response may be a head-mounted eye tracker, such as the Tobii Pro Glasses, a display-mounted eye tracker, such as the Tobii 4C, or an eye tracker integrated into the display device itself, such as the Oculus Rift or Oculus Quest virtual-reality headset.

Numerous variations may be practiced in the preferred embodiment.

BRIEF DESCRIPTION OF THE DRAWINGS

A further understanding of the invention can be obtained by reference to embodiments set forth in the illustrations of the accompanying drawings. Although the illustrated embodiments are merely exemplary of systems, methods, and apparatuses for carrying out the invention, both the organization and method of operation of the invention, in general, together with further objectives and advantages thereof, may be more easily understood by reference to the drawings and the following description. Like reference numbers generally refer to like features (e.g., functionally similar and/or structurally similar elements).

The drawings are not necessarily depicted to scale; in some instances, various aspects of the subject matter disclosed herein may be shown exaggerated or enlarged in the drawings to facilitate an understanding of different features. Also, the drawings are not intended to limit the scope of this invention, which is set forth with particularity in the claims as appended hereto or as subsequently amended, but merely to clarify and exemplify the invention.

FIGS. 2A and 2B depict an example of the Curveball procedure. FIG. 2A depicts a participant engaging with the Curveball task. An eye tracker (e.g., the Tobii 4C) is attached to the bottom of an all-in-one computer, which may be held in front of the participant at 62 cm with an articulated arm. The noise depicted on the computer screen is 1 cycle per degree (CPD). FIG. 2B is a screenshot in accordance with the Curveball task that demonstrates the size and Hann windowing of a noise target. The noise target depicted is 1 CPD.

FIGS. 11A and 11B are graphs depicting a "sweep trajectory" approach to measuring CSFs.

DETAILED DESCRIPTION OF THE INVENTION

Figure 1:
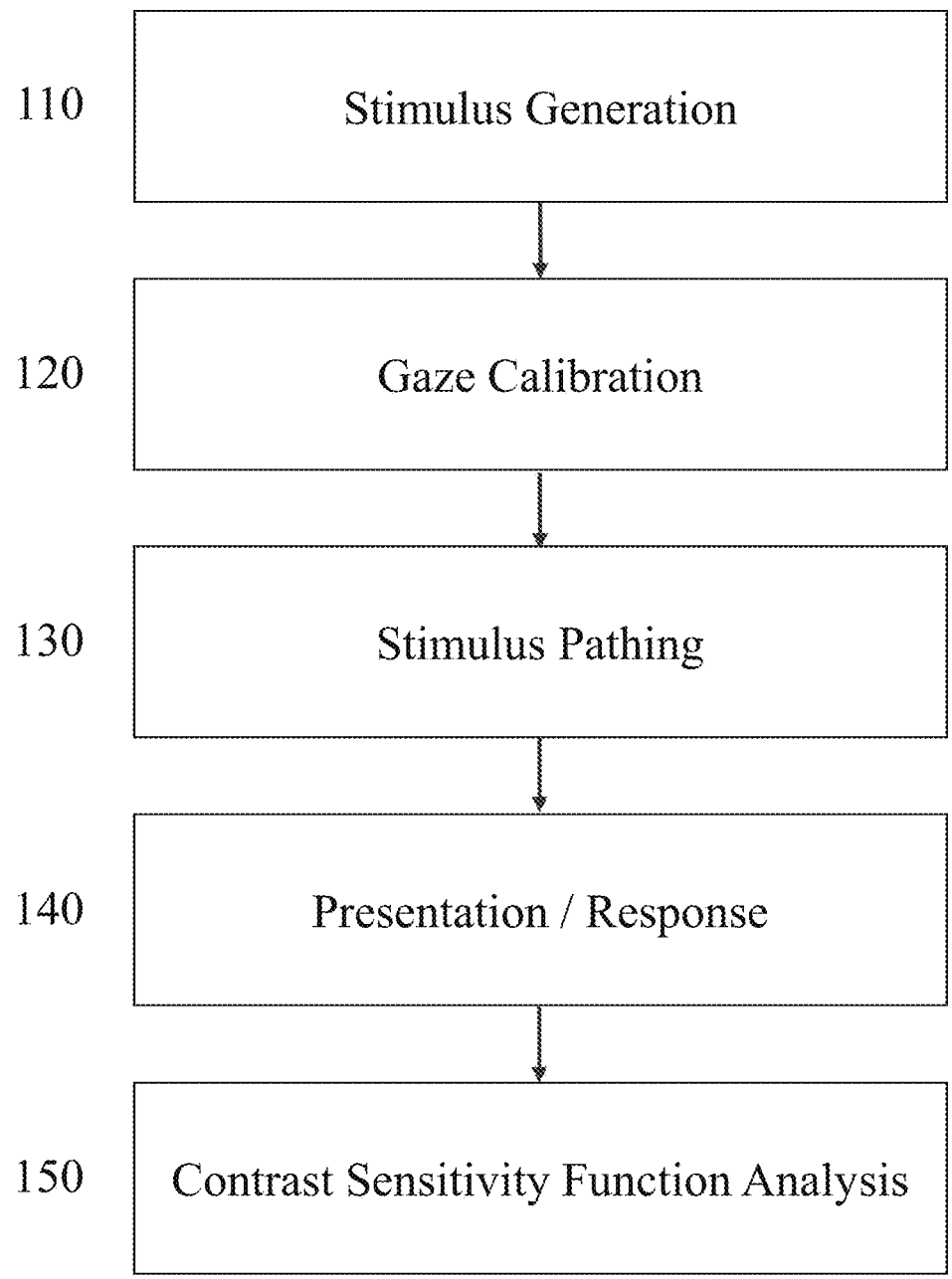
FIG. 1 is a flowchart depicting several steps in an illustrative embodiment of the method of the invention.

The invention may be understood more readily by reference to the following detailed descriptions of embodiments of the invention. However, techniques, systems, and operating structures in accordance with the invention may be embodied in a wide variety of forms and modes, some of which may be quite different from those in the disclosed embodiments. Also, the features and elements disclosed herein may be combined to form various combinations without exclusivity, unless expressly stated otherwise. Consequently, the specific structural and functional details disclosed herein are merely representative. Yet, in that regard, they are deemed to afford the best embodiment for purposes of disclosure and to provide a basis for the claims herein, which define the scope of the invention. It must be noted that, as used in the specification and the appended claims, the singular forms "a", "an", and "the" include plural referents unless the context clearly indicates otherwise.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

A system in accordance with the present invention may include a computer device having a computer processor (CPU) and a non-transitory computer readable storage medium, a display, and an eye-tracking device. The computer device also preferably has a graphics-processing unit (GPU). An example computer device is the 27" widescreen LCD Lenovo Horizon 2 "all-in-one" computer. The memory of the computer device may store software to operate the computer and run the algorithms and other software used during each evaluation. The computer may also be used to process the data generated during each evaluation.

Preferably, the gamma function and the minimum and maximum luminance of the display screen are determined. Screen luminance of the display may, for example, be calibrated with the sRGB profile (gamma of approximately 2.2). Screen luminance may, for example, be measured with an ILT1700 radiometer and may range linearly, for example, from 0.1 (black) to 211.1 (white) $cd/m^2$ with the room lights off (the "dark" condition) and, for example, 10.0 to 221.1 $cd/m^2$ with the lights on (all other conditions). The display may be mounted on a wheeled stand with an articulated arm and equipped with a USB display-mounted eye-tracking device, such as the Tobii 4C eye tracker. The eye-tracking device may be capable of detecting the gaze position of one or of both eyes simultaneously. The Tobii 4C has an operating distance of 50 to 95 cm and samples mean gaze position at 90 Hz by combining data from both eyes.

The Curveball algorithm may be programmed in any one of a variety of coding environments. For example, the stimulus behavior may be programmed in Python using the Shady graphics toolbox and may be updated and rendered at a frame rate of 60 Hz. Gaze data may be analyzed in real time using the Curveball algorithm, which measures the similarity between gaze and stimulus trajectories to infer stimulus visibility on a frame-by-frame basis.

Each evaluation may begin with a calibration phase, which may include the sudden presentation of an image in the center of the display. Alternatively, multiple images may be presented on the display. For example, one image in each corner of the screen. Each image may be, for example, a white disc with a plurality of dark circles. The image may be presented against a uniform gray background (e.g., value of 0.5), and that same background may be used for the subsequent trial phase. The image may be designed to draw the participant's gaze to a central calibration point without explicit instructions. The image may also be rotated, for example, with increasing angular velocity as the participant looks at the image (e.g., within 8° of visual angle (hereafter simply °) of its position). This calibration phase may calibrate for any small offset in gaze position, and may be used to ensure that the participant is looking at the display before launching the main task. After a predetermined period of time, such as 0.5 seconds of calibration, the disc may fade out and the trial phase may begin.

At the start of each trial, one or more stimulus images (also referred to herein as noise targets), such as a narrow-band frozen noise patch subtending 12°, may appear at a random location on the screen. The stimulus image may then move around the display. The stimulus image may continuously veer clockwise or counter-clockwise in a sequence of smooth random turns. Alternatively the stimulus image paths may be procedurally generated by an algorithm. For example, the stimuli may move within an invisible grid, may avoid collisions with other stimuli by not moving to grid cells that are currently occupied, and may avoid repeating the same type of movement twice in a row and/or making the same type of concurrent movement as other active stimuli. The initial positions of the stimuli may be predetermined or random, with or without additional restrictions (e.g. preventing multiple stimuli from appearing at the same location).

The stimulus image may maintain a fixed speed of, for example, 10° per second, or the speed at which the stimulus image moves on the screen may vary. For example, the speed of the stimulus image may increase at a constant rate, or the speed of the stimulus image may decrease at a constant rate. The speed of the stimulus may change throughout the path and/or vary both between and within method applications as a function of participant responses or to facilitate different measurement needs or display devices. For example, stimuli may move at 10 degrees per second on a larger display when following a straight path, but decrease in speed to 8 degrees per second when following a curved path.

The stimulus image may be generated by applying a circular-symmetric Hann window to a filtered noise pattern that may be re-generated with a new random seed for each trial. The noise may start off with a 1/f amplitude spectrum in the frequency domain and a random phase spectrum. It may then be filtered with an annular band-pass filter centered on the target spatial frequency. The minimum and maximum bounds of the filter may be computed by multiplying and dividing the target spatial frequency by 0.9, respectively, which may gave the filter a width of approximately 0.34 octaves. The resulting noise would then have equal power at all orientations but may be limited to a narrow band of spatial frequencies.

Temporal aliasing at high spatial frequencies may be prevented by applying an additional anisotropic filter to the amplitude spectrum of the noise. This filter may remove all components with horizontal spatial frequency greater than 2.85 CPD, which is 95% of the Nyquist limit (3 CPD) of a stimulus moving at 10° per second on a display with a refresh rate of 60 Hz. Different anisotropic filters may be applied at different stimulus speeds as the Nyquist limit changes. The orientation of the noise patch may be continuously steered into its direction of motion to keep the anti-aliased direction of this filter "facing forward" at all times.

The noise target may sharply rebound whenever it collides with the edge of the screen and may be simultaneously rotated by 180° to continue "facing forward." Rapid variation in stimulus position and rotation may also help ensure that it is presented at all orientations in all regions of the screen within a single trial. The stimulus image size (e.g. 12°) may be chosen to make it large enough to display the lowest spatial frequency in the procedure (e.g., 0.25 CPD) whilst being small enough that its rotation does not interfere with the pursuit detection algorithm if a participant happens to fixate away from its center (where target rotations produce transient higher gaze velocities). Its size may be fixed across all spatial frequencies to avoid changing the difficulty of tracking. A screenshot with the target at high contrast is depicted in FIG. 2B.

At the start of each trial, one or more noise targets may be displayed. The noise target may be generated at the start of each trial. In the alternative, one or more noise targets may be generated and stored in memory in advance of the evaluation, and the software may retrieve the one or more noise targets from memory at the start of each trial.

Figure 2C:
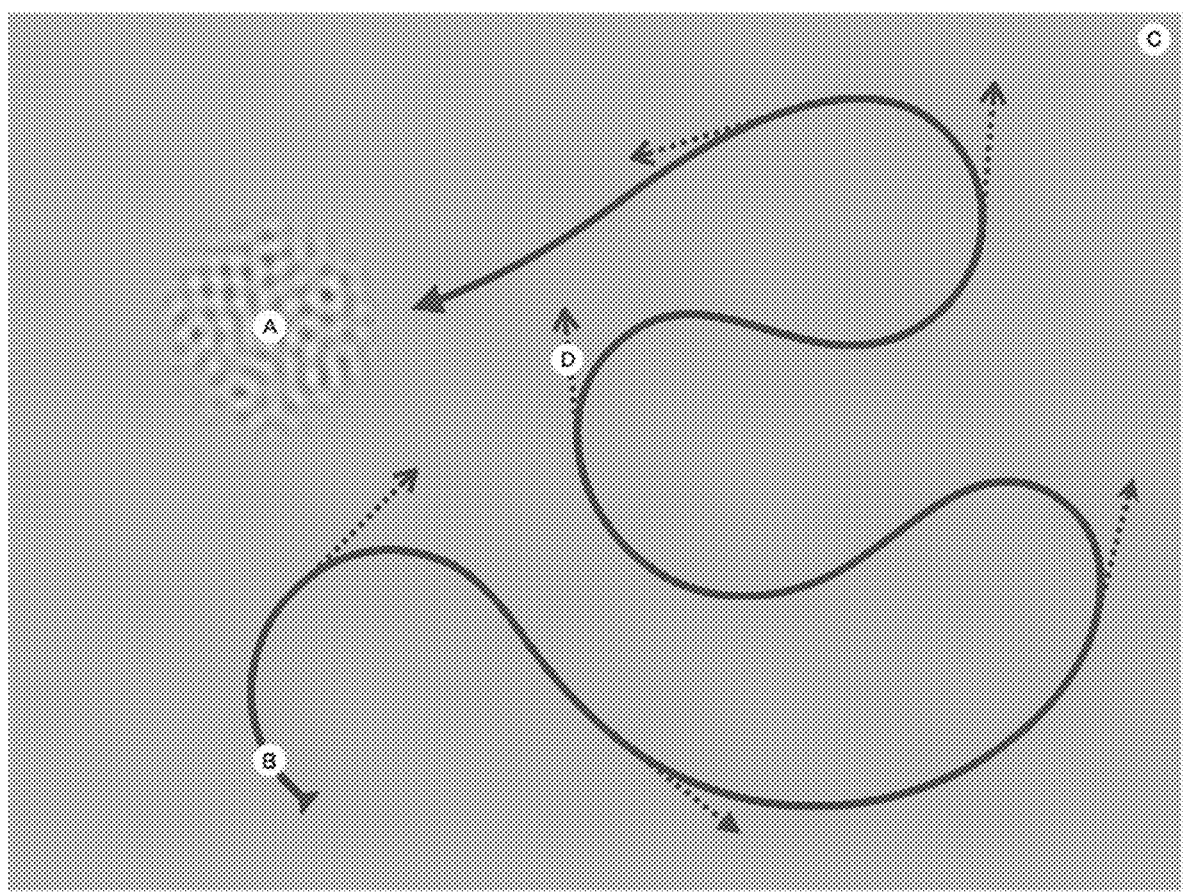
FIG. 2C depicts an exemplary Curveball stimulus presentation in accordance with the present invention.

Referring to FIG. 2C, a circular noise stimulus (A) may move smoothly on a haphazard path (B) across a computer screen (C). Isolated circular patches of similarly band-filtered noise may be displayed as the stimulus. These 'curveball' stimuli (each with a single fixed spatial frequency) may be presented one at a time. The stimuli may drift randomly across the display in all directions. The stimuli may drift at constant speed or variable speed. The stimuli may rebound whenever they hit the edge. Eye movements that match the speed and direction of each stimulus with high adherence may provide evidence of stimulus visibility. Since such smooth eye movements are difficult to produce without the stimulus being present on the retina, eye movements that do not follow the stimulus in the course of testing (D) may provide evidence that the stimulus is not visible. Computer software comprising a computer algorithm may compare the recent trajectories of the stimulus and the observer's gaze to detect tracking, rather than relying solely on a velocity match. The software may require the observer to match the speed, direction, and approximate position of the stimulus at all times to satisfy the algorithm, which is next to impossible when the stimulus is not visible. Successful tracking may cause the contrast of the stimulus to continuously decrease in real time as long as the stimulus is tracked. The trial may terminate when the stimulus is no longer tracked. A threshold estimate may be provided from the trial.

Stimuli with higher spatial frequency may be filtered in one direction (while maintaining the specified contrast value) to avoid temporal aliasing caused by the texture's motion. Each stimulus may rotate as it changes direction to ensure that the direction of the anisotropic filter is always oriented to match the direction of motion.

Thresholds may be estimated one or more times at multiple different spatial frequencies. A curve may then be fitted to the final set of thresholds to estimate the observer's CSF. For example, four repeats may be performed for each of six spatial frequencies.

Figure 2D:
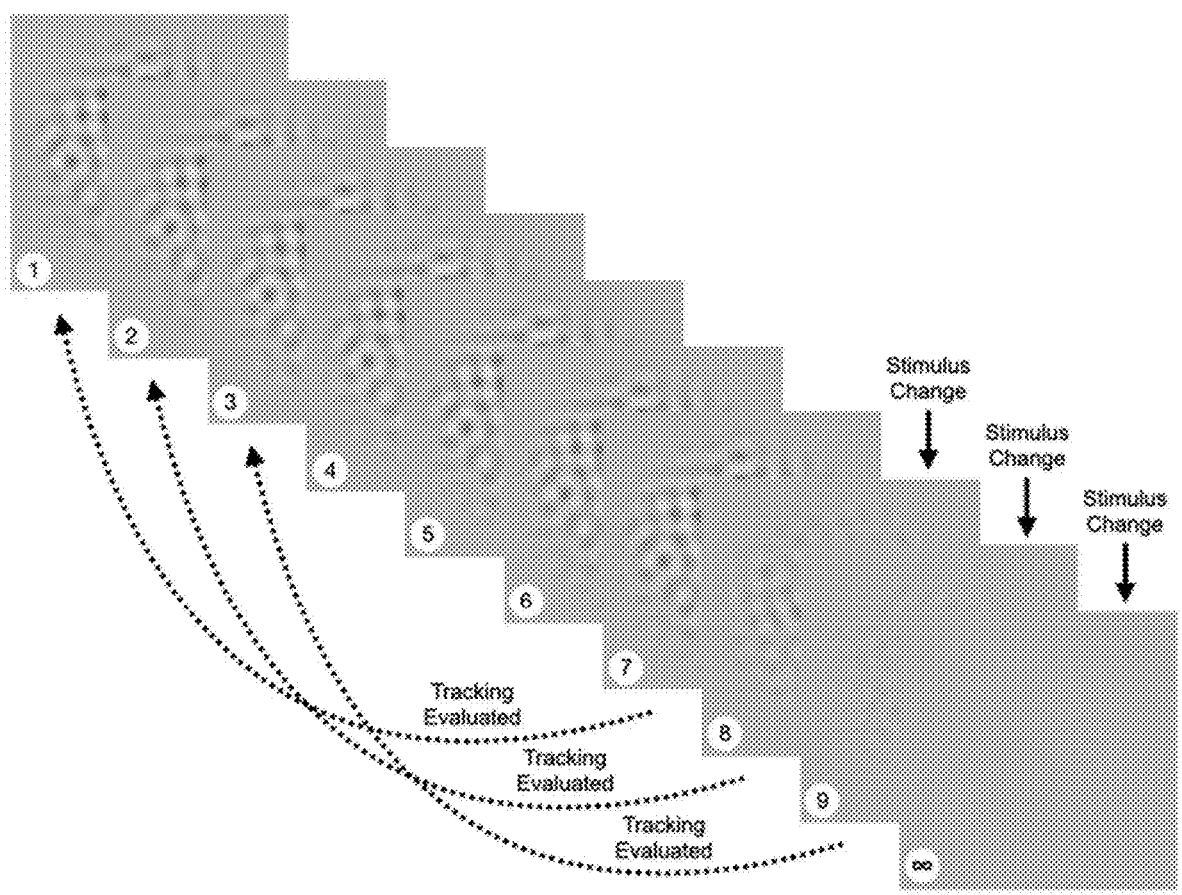
FIG. 2D depicts an exemplary methodology for manipulating stimulus contrast based on stimulus tracking.

Referring to FIG. 2D, an algorithm running may infer or estimate stimulus visibility through smooth eye-tracking in a frame-by-frame manner with a gaze-stimulus trajectory match computed over a sliding time window. Based on the trajectory match computed over the past few frames (exemplary number of frames shown in the lower left corner of each frame), stimulus contrast may be lowered in real time using, for example, GPU shaders until a threshold is identified. For example, after evidence of compliant tracking over 7 sequential frames (line with arrow linking frame 7 and frame 1), contrast may be decreased on the 8th frame. If compliant tracking is again present since frame 2, stimulus contrast may be adjusted down on frame 9. That pattern may be followed until compliant eye movements are no longer present and the trajectory match continually fails over a short time interval. The final stimulus contrast provides a provisional estimate of minimal contrast visibility.

Figure 2E:
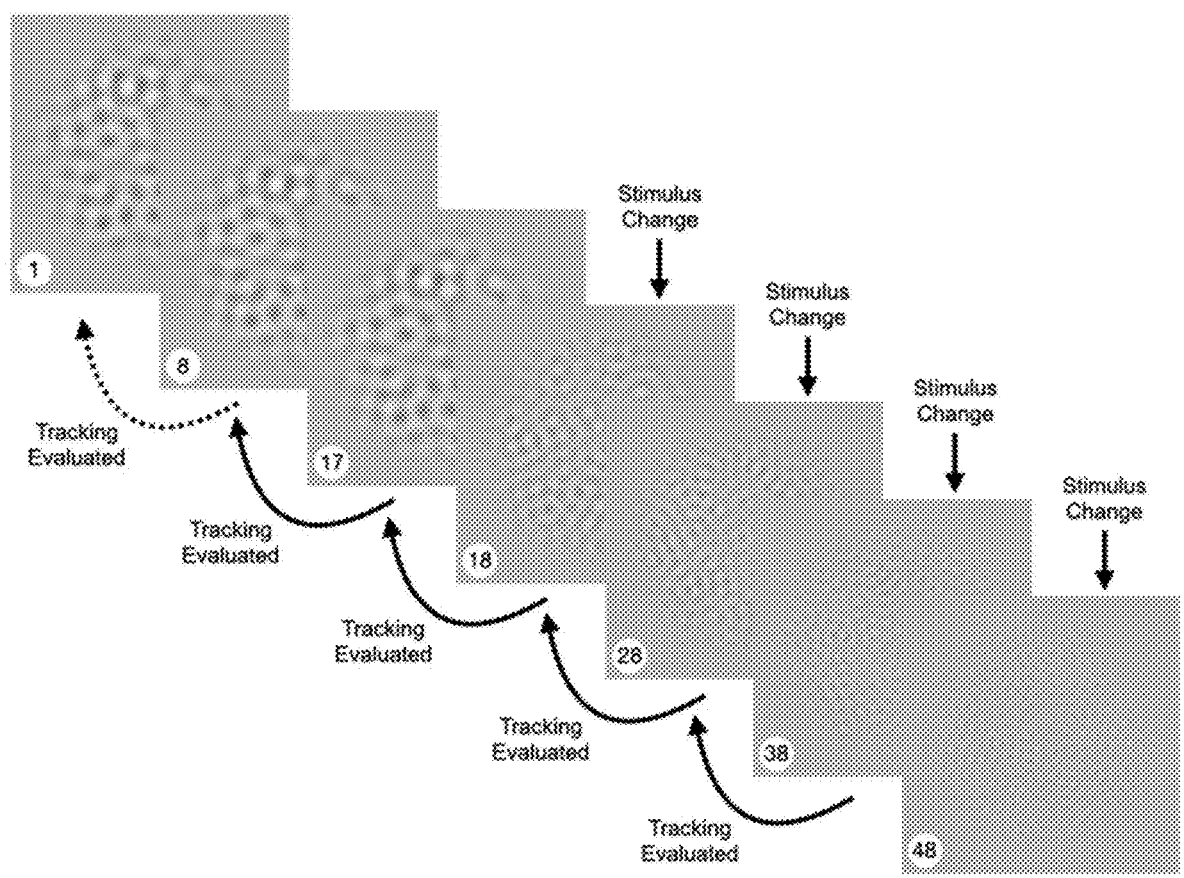
FIG. 2E depicts an exemplary methodology for simultaneously manipulating stimulus contrast and spatial frequency based on stimulus tracking.

Referring to FIG. 2E, a software algorithm may infer or estimate stimulus visibility through smooth eye-tracking in a frame-by-frame manner with a gaze-stimulus trajectory match computed over a sliding time window. Compliant tracking may be detected based on a trajectory match computed over some number of most recent sequential frames (e.g. 8) that display the same originating stimulus (frames 1-8, dotted line with arrow). If this sliding-window algorithm detects compliant tracking for a sufficient number of frames in a row (e.g. 10; solid lines with arrows), stimulus visibility may be inferred, and stimulus contrast and spatial frequency are made less visible on the following frame (i.e. 18). This process of inferring stimulus visibility (and changing the stimulus properties) after a predetermined number of frames (e.g. 10 frames) of compliant tracking may continue until tracking is no longer detected by the sliding-window algorithm for a predetermined longer duration (e.g. 180 frames). If tracking is continuous as the stimulus changes, the initial build-up of tracking evidence (frames 1-8) may not re-occur. The final stimulus contrast/spatial frequency combination may provide a provisional estimate of stimulus visibility.

Additional images, animations, and/or videos may be presented in tandem with the noise target(s) or between trials to facilitate task attention or provide a reward or break to the participant. The images may be, for example, semi-transparent textures superimposed on the moving noise target to quickly draw a participant's attention to the noise target. For example, a cartoon ghost may appear on top of the stimulus at the start of each trial to draw the observer's gaze, and then disappears upon initial fixation. The assistive image may fade out as soon as the participant's gaze comes within, for example, 5° of the image. As a further example, one or more images or animations (e.g., animated fireworks) may, for example, appear as a visual reward for a predetermined amount of time (e.g., two seconds) at the end of a trial or when a certain duration or quality of pursuit behavior is detected. As a further example, a video may be played on the computer screen between trials to provide the participant with temporary relief from the task. These images, animations, and videos may or may not include audio content.

After the semi-transparent image fully disappears, the Curveball algorithm may begin searching for smooth pursuits by continuously comparing the recent 2D trajectories of the participant's gaze and the positions of the noise target on the screen. This may be accomplished by examining the trajectory of the target over a number of recent frames (e.g., eight frames) and translating this trajectory to the current gaze position on the screen, which will generate an expected gaze trajectory. Gaze position may first be filtered with a real-time noise removal algorithm that detects and discards estimates of gaze position from the eye tracker that are not consistent with the known limits of human behavior, such as eye movements that are impossibly fast. A tracking 'hit' may be recorded if the most recent gaze position is within some allowed distance (e.g., 1°) of the stimulus center and each point in the recent gaze trajectory is within some allowed distance (e.g., 0.4°) of the corresponding point in the expected trajectory. The algorithm's precise trajectory length and error tolerance may be determined through empirical analysis of the particular eye tracker used (e.g., the Tobii 4C). After a predetermined number of frames (e.g., five frames (83 ms)) of consecutive smooth pursuit "hits" (i.e., the gaze of the participant matches the movement of the noise target), the root mean-square (RMS) contrast of the noise target may decrease, for example, logarithmically. The contrast may decrease as long as smooth pursuit hits continue.

The starting RMS contrast of the noise may be, for example, 0.317; this contrast may be above the maximum contrast (—0.22) that can be displayed on a particular monitor without clipping, but it may be chosen for maximum initial visibility. Every frame of ongoing pursuit may cause its RMS contrast to be multiplied by a predetermined amount, such as 0.97. If a participant stops pursuing the target for a predetermined number of consecutive frames (e.g., one frame, five frames, or 10 frames), the contrast reduction may be halted. The algorithm may then wait for a predetermined number of consecutive frames of pursuit (e.g., one frame, five frames, or 10 frames) before resuming the trial. Contrast may increase and decrease during a trial. In the alternative, contrast may never increase during a trial. Participants may instinctively follow the target's motion on each trial until it fades beyond their threshold, which typically takes up to ten seconds, depending on a participant's sensitivity to a particular spatial frequency and the consistency of their smooth pursuits.

The trial may be terminated according to a continuously updated deadline. For example, every trial may start with a trial duration (i.e., "lifespan") of three seconds starting from the moment the semi-transparent image fully disappears. The lifespan may be increased by six frames (0.1 seconds) every time a frame of smooth pursuit occurs. Participants may therefore need to pursue the target for at least one in every seven frames, on average, to prevent the trial from terminating. When the lifespan expires, the reciprocal of the noise target's final RMS contrast in each trial may be recorded as a sample of the contrast sensitivity threshold at that target's spatial frequency. If the final RMS contrast value is above the value where the stimulus pixel intensities went out of range (e.g., ~0.22), no threshold may be recorded. Less than 0.25 seconds of tracking may be needed to reduce the target's contrast below this value. The next trial may immediately begin with full contrast, a new noise target, and/or semi-transparent image.

Each participant may, for example, complete four repeats of six spatial frequencies in a full Curveball run. The spatial frequency values may be equally spaced in log units: 0.25, 0.5, 1, 2, 4, and 8 CPD. The lowest two contrast thresholds for each spatial frequency may be averaged to determine the final threshold estimates. This may account for participants 'dropping' trials due to false negatives, which could be caused by inattention, poor or infrequent tracking, or other reasons. In lieu of a systematic way of detecting these false negatives, the worst (highest) threshold estimates (e.g., the worst 50% of threshold estimates) may be discarded to remove them. The twenty-four noise patches required may be generated on the CPU as the task is initialized, but their visibility, contrast, windowing, gamma-correction, 'noisy-bit' dithering and position may be processed in real time, for example, with a GPU using the Shady graphics toolbox. The efficiency of the GPU operations may ensure that the task runs at a consistent frame rate of 60 Hz. In total, a full run of Curveball may take an average time of 5 minutes and 15 seconds (standard deviation of 37 seconds) across all observers and conditions.

The Curveball algorithm requires participants to smoothly pursue the noise target, and this pursuit behavior must be of sufficient quality to be distinguished from other eye movements (such as saccades) that provide much weaker evidence about target visibility. If a participant cannot pursue a given target smoothly enough to meet the algorithm's minimum requirement, the trial will end prematurely and their sensitivity to that target's spatial frequency will be underestimated (a false negative).

Figure 3:
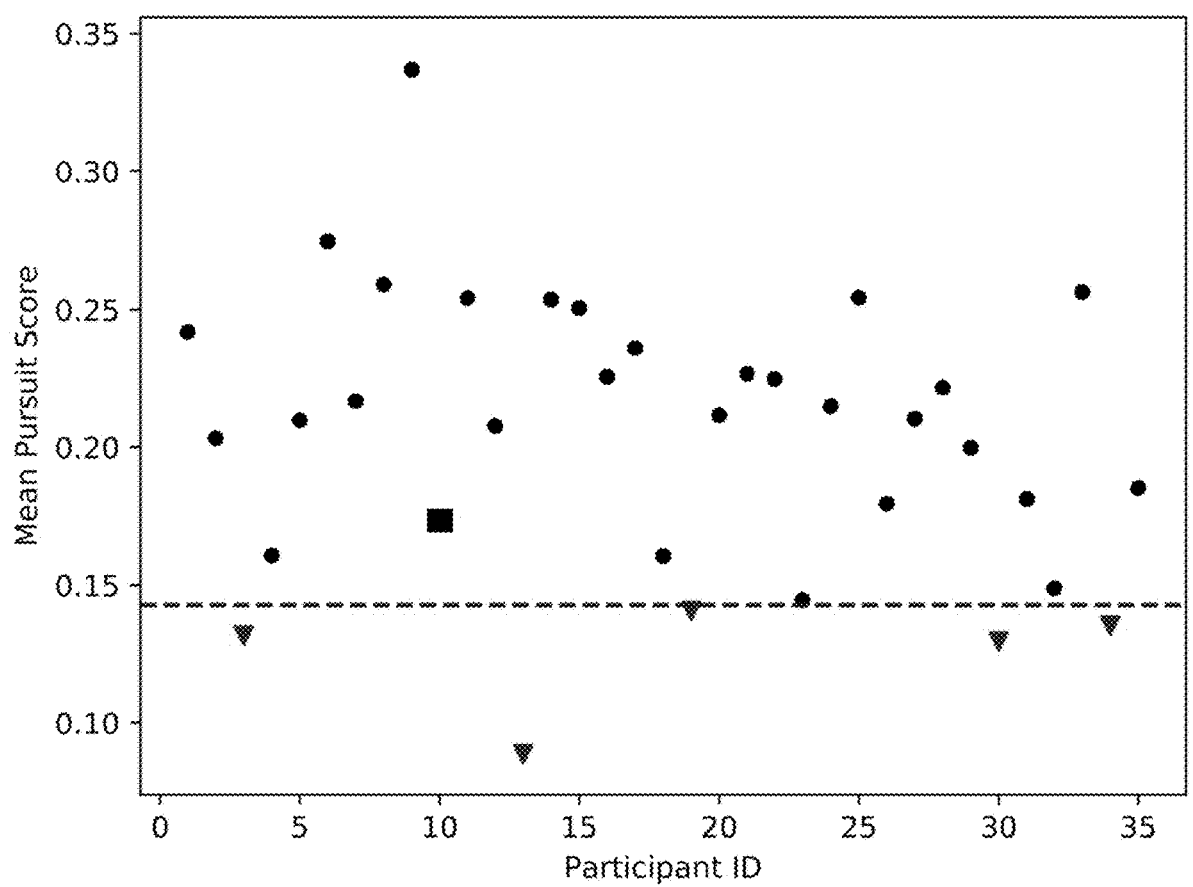
FIG. 3 depicts Scatterplot of Curveball mean pursuit scores. The dashed line (pursuit score=0.143) depicts the minimum pursuit score required for inclusion in the CSF results. Participants marked by red triangles fell below this threshold and were excluded from all analyses. The red dot represents a participant who was independently excluded due to an incompatibility between their asymmetric corrective lenses and the eye tracker.

Curveball's analysis protocol may account for 'dropped' trials by discarding the worst half of thresholds obtained for each spatial frequency (two out of four). Some participants, however, may still track the target too poorly overall to compute any accurate or consistent estimate of sensitivity. These participants may be identified by calculating the overall proportion of frames in which each participant met the Curveball criterion for smooth pursuits over all runs and conditions of the task (the "pursuit score" for that participant). Sample overall mean pursuit scores for participants are depicted in FIG. 3. Five participants were excluded due to having an overall mean pursuit score below 0.143, i.e. one out of seven frames (triangles below the dashed line in FIG. 3). This was a predetermined minimum tracking score required to prevent the Curveball trial from terminating. These additional exclusions are noted in the analyses below and the excluded threshold data are faded in corresponding figures. The reliance of Curveball on smooth pursuit ability is discussed in further detail below.

One additional participant (square in FIG. 3) was excluded because the eye tracker had difficulty integrating the gaze estimates from the participant's left and right eyes, which was likely due to strong asymmetric correction for a large astigmatism (cylindrical power of OD −1.25, OS −5.75). This problem can be avoided by only taking monocular measurements for participants with incompatible eyewear. Other participants with smaller correction for astigmatism or bifocal lenses are not affected.

The Curveball procedure depends on a minimum quality of smooth pursuit ability, but the contrast sensitivity thresholds it produces should not be strongly dependent on the precise quality of each participant's smooth eye movements beyond the required amount. This would suggest that the Curveball task was effectively only measuring smooth pursuit ability. This possibility was tested by regressing mean sensitivity across the standard Curveball runs on pursuit ability.

Figure 4:
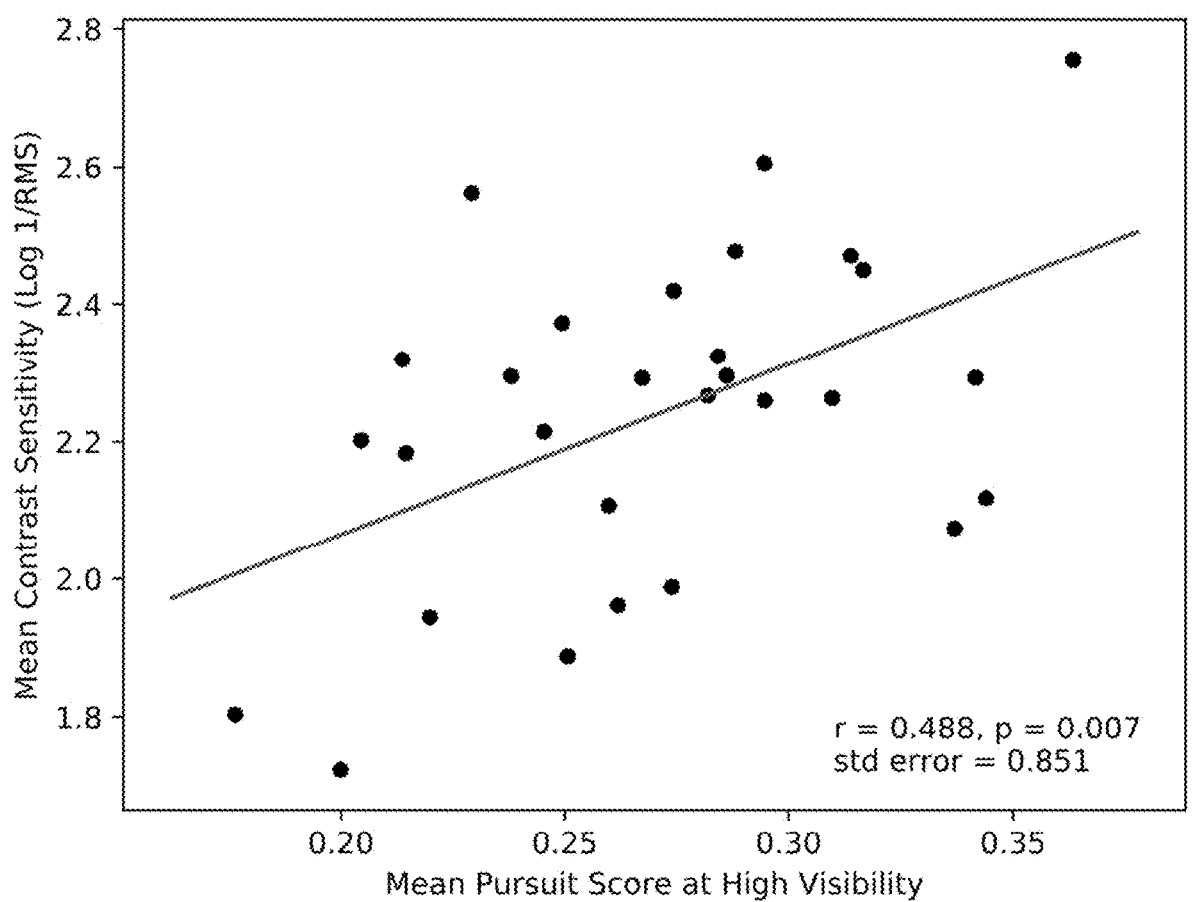
FIG. 4 depicts a regression plot of mean contrast sensitivity against mean pursuit score for high-visibility stimuli. Each point represents a different participant. Sensitivity and general pursuit ability were moderately correlated.

Mean sensitivity will naturally be related to overall pursuit score, as participants with better contrast sensitivity spend a greater proportion of time tracking the noise target instead of waiting for trials to terminate. This conflating factor may be accounted for by only examining pursuit scores from periods in which the noise target was likely to be visible to all participants: a spatial frequency of 1 CPD (the peak sensitivity for most participants) and RMS contrast of 0.01 or greater (log sensitivity of 2). FIG. 4 depicts mean contrast sensitivity over three standard Curveball runs (vertical axis) against this high-visibility pursuit score (horizontal axis) for each participant. A linear regression revealed that mean sensitivity was weakly but significantly predicted by this tracking score, $r=0.488$, $p=0.007$, with a large standard error of 0.851 log units of sensitivity (approximately half the height of a typical CSF curve). This indicates that participants who were better at smoothly tracking a highly visible target tended to achieve better contrast thresholds, but not to a strong degree. Participants who were better at tracking the target may have been slightly more likely to continue tracking for a short interval after its contrast was reduced below threshold (but before the target could change direction). Alternatively, smooth pursuit ability and mean contrast sensitivity may be inherently related through some measure of general visual function.

Figure 12:
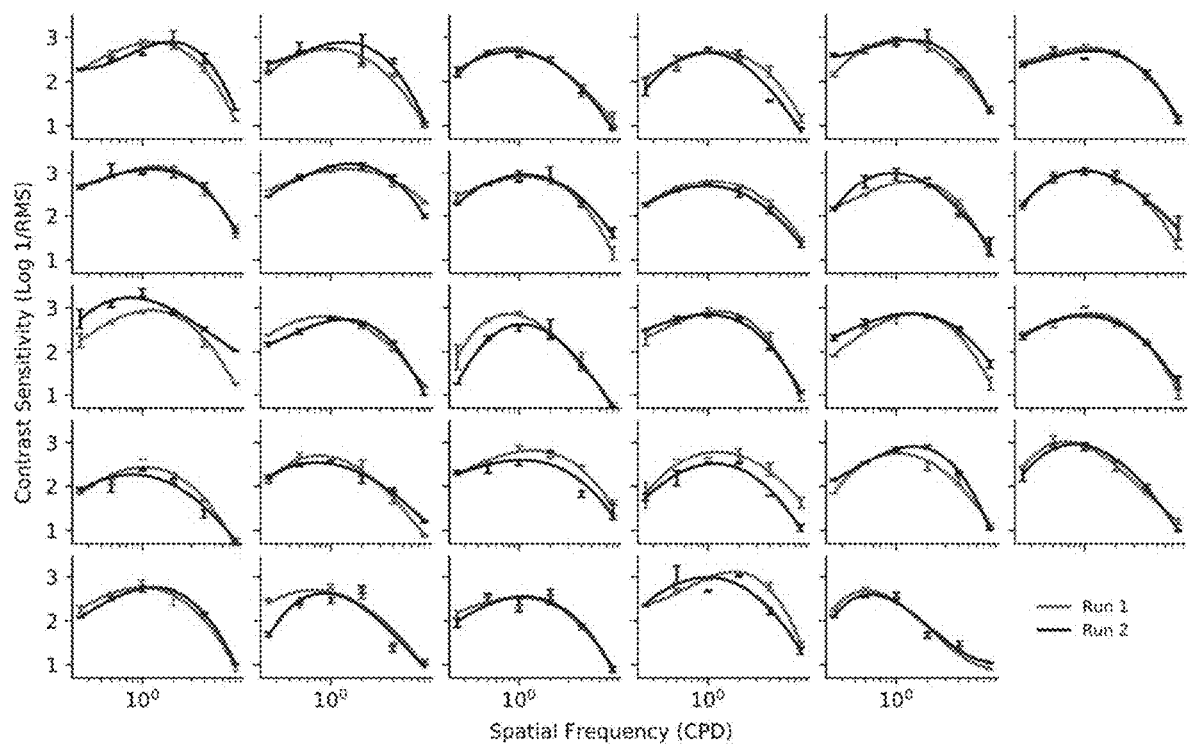
FIG. 12 depicts same-day repeatability of Curveball mean thresholds. Each subplot depicts the CSFs for a participant obtained from the first (blue) and second (purple) Curveball runs within the first testing session. Horizontal axes represent spatial frequency in log scale and vertical axes represent log units of RMS contrast sensitivity. In this and subsequent figures, error bars represent ±1 SEM and the smooth curves correspond to the optimal cubic polynomial fits.

The same-day repeatability of the standard Curveball task was analyzed by comparing thresholds estimated during a first Curveball run (performed before the 4AFC staircases) and a second (performed after) in the first experimental session. These thresholds are plotted together for each of the twenty-nine included participants in FIG. 12. The horizontal axis in each subplot represents spatial frequency on a log scale and the vertical axis shows log 10 units of RMS contrast sensitivity. The limits and scale of the axes are identical in each subplot. All future figures of CSF data have the same layout and axes as FIG. 12.

Figure 5A:
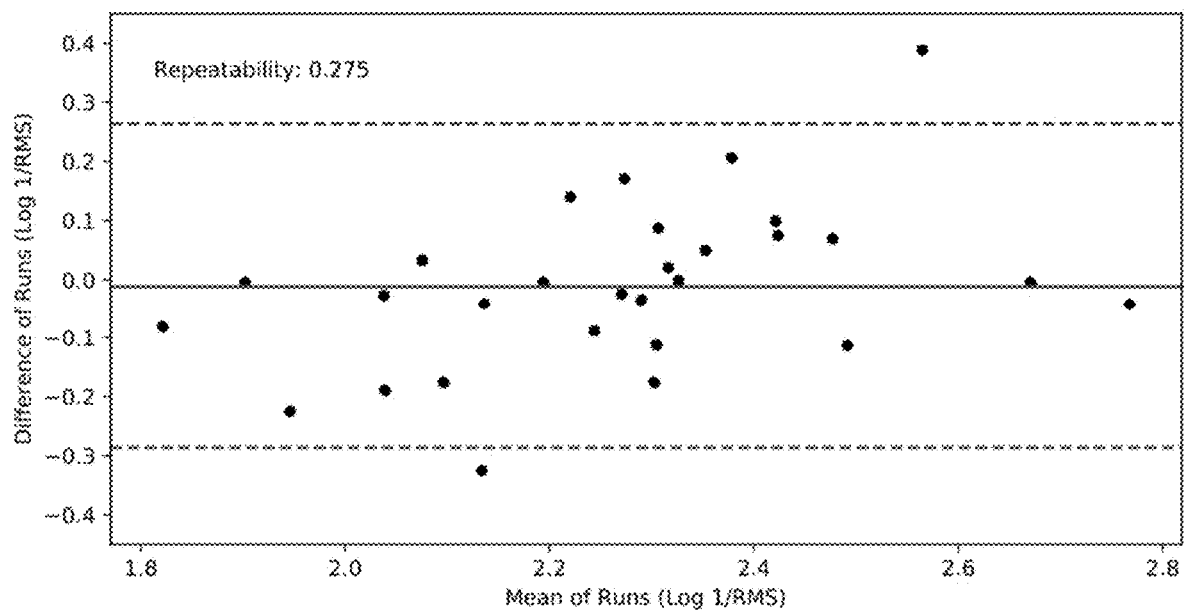
FIGS. 5A and 5B depict Bland-Altman plots for same-day and different-day repeatability, respectively. The first standard Curveball run from the first testing session has been compared with the second run from the same session (FIG. 5A) and the standard run from the second session on a different day (FIG. 5B). The vertical and horizontal axes represent the difference and mean of the two conditions compared in each case. The coefficient of repeatability in log units of sensitivity is depicted in the top-left of each plot. The solid black line marks the mean difference and the dashed lines represent the 95% limits of agreement (mean±coefficient of repeatability).

Same-day repeatability can be visualized in the Bland-Altman plot depicted in FIG. 5A. This figure depicts the difference in mean sensitivity between Curveball runs for each participant plotted against the mean of the two runs. The horizontal lines represent the 95% limits of agreement. The same-day coefficient of repeatability was 0.275 log units of RMS contrast sensitivity. A substantial proportion of the same-day variance was contributed by one participant who performed much better on their second run of the task (uppermost data point in FIG. 5A). The coefficient of repeatability decreases to 0.236 if this outlying participant is discounted.

Figure 5B:
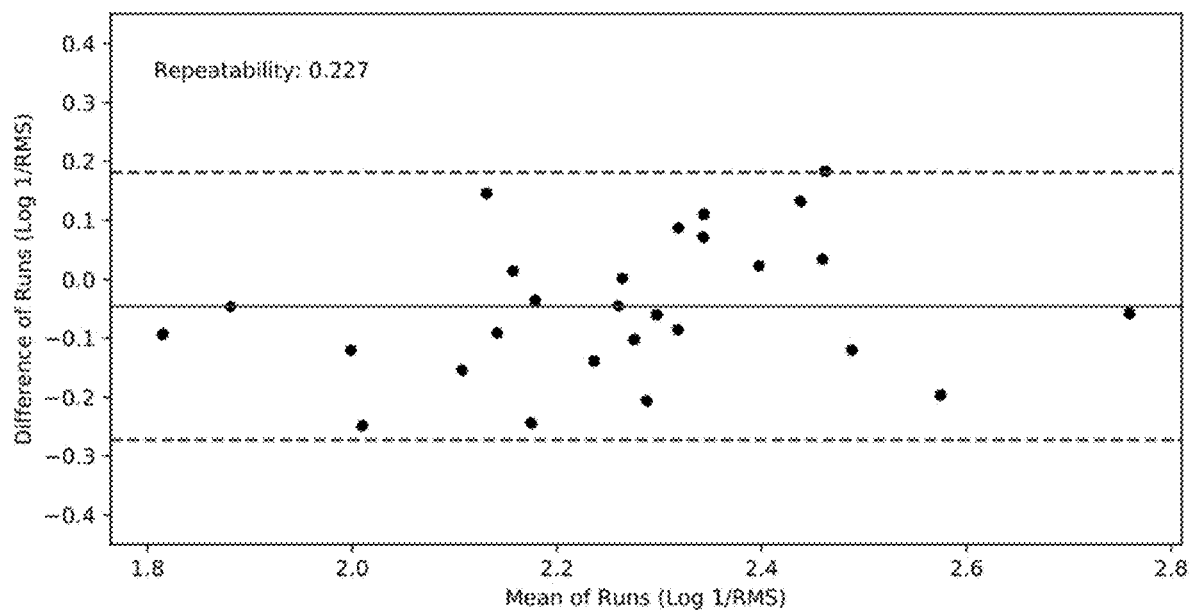
Figure 13:
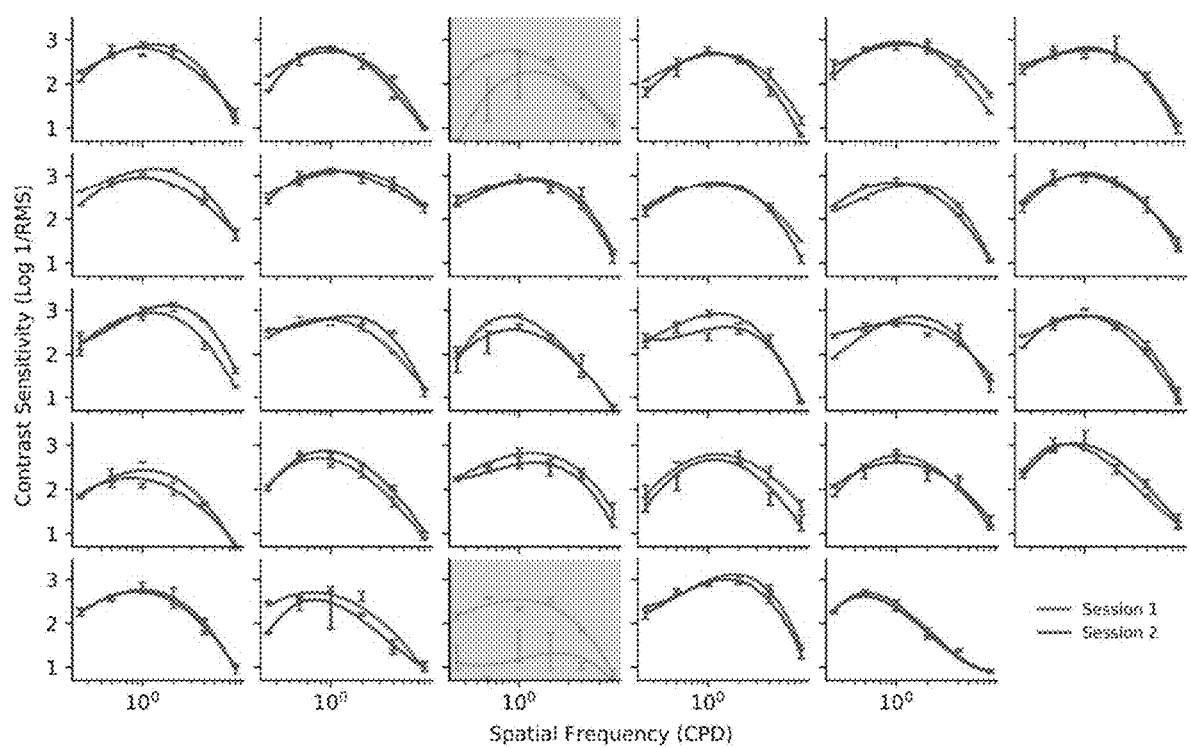
FIG. 13 depicts different-day repeatability of Curveball mean thresholds. The layout is identical to FIG. 4, but the lines now represent mean sensitivity in the first (blue) and second (green) testing sessions. The faded subplots represent two participants whose pursuit scores were below the exclusion threshold in the second session's standard Curveball run.

Different-day repeatability was analyzed in an analogous way to same-day repeatability. Thresholds from the first Curveball run in the first session were compared against thresholds from the standard Curveball run in the second experiment for each participant (FIG. 13). The faded subplots indicate two participants whose ability to smoothly pursue the stimulus fell below the exclusion threshold in the second session, which led us to exclude them from this analysis. The coefficient of repeatability was 0.227 log units of sensitivity, as shown in the Bland-Altman plot depicted in FIG. 5B, which is similar to the same-day repeatability. There was no significant correlation between mean sensitivity in the second session's run and the run's position (from first to fourth) in the random ordering of conditions in the second session, $r=0.025$, $p=0.897$, which suggests that participants did not become noticeably fatigued during the second session. Overall, our analysis indicates that Curveball is a highly repeatable measure of contrast sensitivity, both within a single testing session and across different days.

If Curveball is a valid measure of contrast sensitivity, the CSFs formed from its thresholds at different spatial frequencies should correspond closely to the CSFs assessed using conventional report-driven psychophysics. This relationship was tested by comparing CSFs estimated using Curveball with CSFs obtained from the traditional 4AFC staircase task completed in the same session. Separate analyses were conducted for the static and moving gratings in the 4AFC task. One participant was excluded from the comparison with the static 4AFC thresholds due to a sensitivity outlier at 2 CPD, which was likely produced by a run of false positives from correct sub-threshold guesses.

Figure 14:
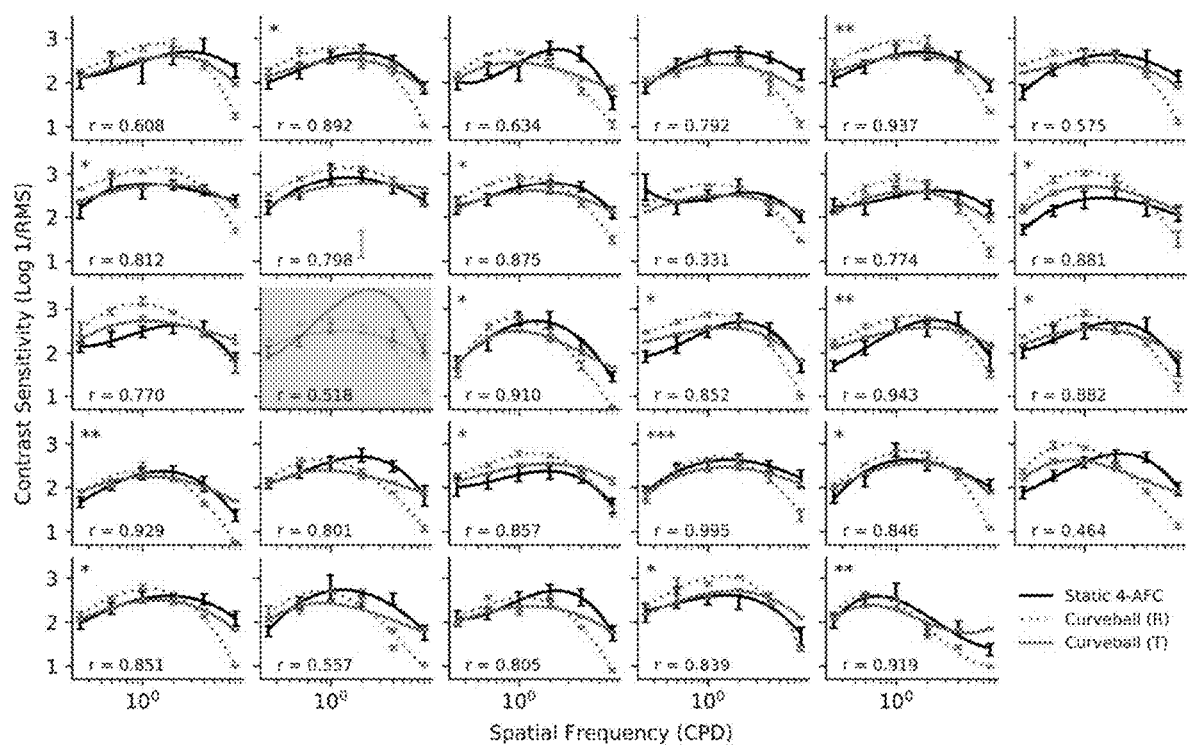
FIG. 14 depicts Curveball thresholds vs. static 4AFC thresholds. The layout and axes are identical to FIG. 12. The dotted and solid blue lines represent the raw and transformed Curveball CSFs, respectively, and the black lines represent the CSFs estimated from the static gratings in the 4AFC staircase task. The faded subplot in the third row denotes one excluded participant who achieved an impossible threshold at 2 CPD in the staircase task. This excluded data was not used to optimize the free transformation parameters for the other participants. Error bars in the 4AFC data here and in FIG. 8 represent ±1 SEM, which was computed using the last four between-reversal runs of each contrast staircase.

The correlations between the raw Curveball thresholds and static 4AFC thresholds are only moderate (mean correlation of 0.681±0.170), but this is not surprising: past work has shown that the CSF elicited by moving stimuli is shifted down in spatial frequency (i.e. horizontally to the left) relative to the CSF for static stimuli. This shift in peak sensitivity may be accounted for by allowing the Curveball thresholds to differ by up to an affine transformation. The scaling, shearing, and vertical offset parameters of the transformation for each participant were optimized over the pooled thresholds from the remaining twenty-seven participants (i.e. a 'leave one out' model). The raw (dotted blue) and transformed (solid blue) Curveball thresholds are plotted together with the static 4AFC thresholds (black) in FIG. 14. The affine transformation significantly improved the mean correlation across participants to 0.790±0.154, $t(27)=4.044$, $p<0.001$. This indicates that the global affine transformation captured a large systematic difference in threshold estimates between the Curveball task and static 4AFC task, and that this difference comprised a large proportion of the between-task variance.

Figure 15:
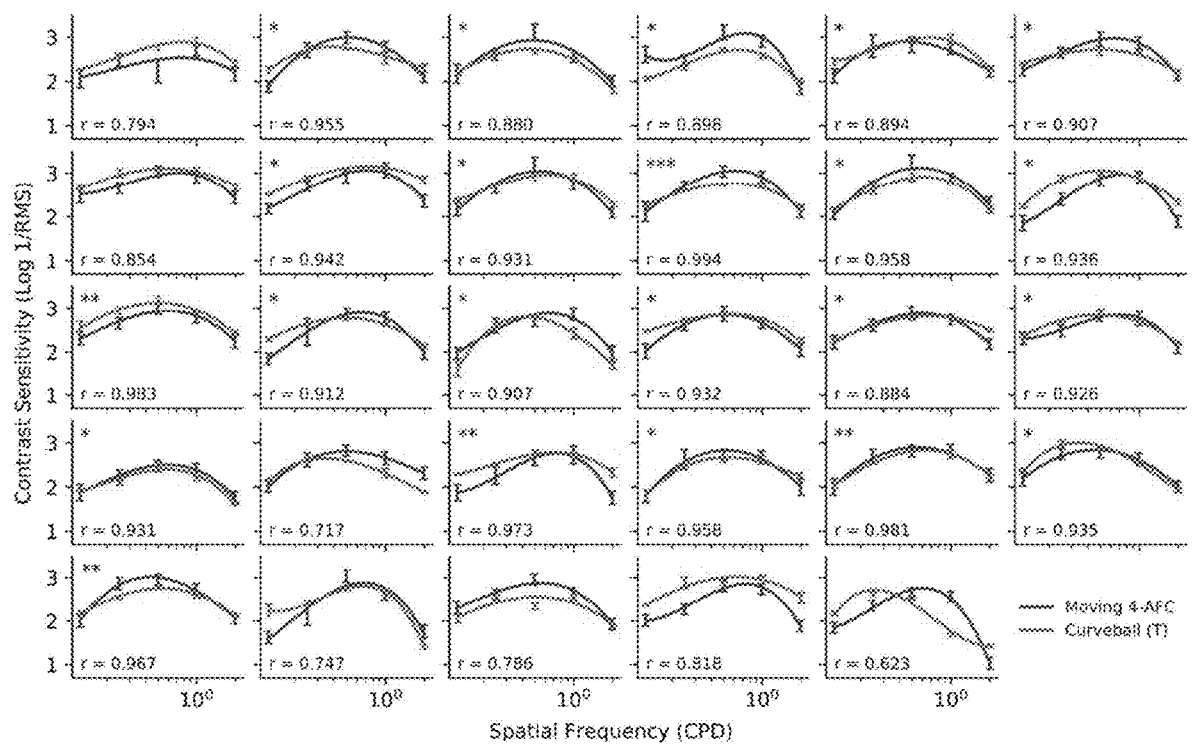
FIG. 15 depicts Curveball thresholds vs. moving 4AFC thresholds. The layout is identical to FIG. 7, but the horizontal axis of each subplot has been shifted to accommodate the lower range of spatial frequencies. The black and blue lines represent the CSFs estimated from moving gratings in the 4AFC staircase task and noise patches in Curveball, respectively. The Curveball spatial frequencies have been reduced by one octave, and the highest value removed, to account for the systematic horizontal shift in the CSF between tasks. No additional participants were excluded from this analysis.

The moving gratings in the 4AFC task were necessarily from a lower and more restricted range of spatial frequencies than the static gratings in the same task (which were not aliased by motion) or Curveball noise patches (which were filtered to avoid temporal aliasing). We accounted for this difference before comparing the moving 4AFC thresholds and Curveball thresholds by simply translating the Curveball thresholds to the left by one log unit (i.e. halving each spatial frequency) and dropping the highest Curveball spatial frequency. This transformation alone was sufficient to determine that the shapes of the Curveball CSFs were highly correlated with the CSFs estimated from the moving gratings in the 4AFC (FIG. 15). The mean correlation was 0.907±0.074 and was significant at the 0.05 level for nineteen out of twenty-nine participants. Allowing for an additional global affine transformation in the same way as the static gratings had no significant impact on these correlations, $t(28)=-1.116$, $p=0.274$.

Overall, these analyses indicate that CSFs obtained using Curveball are well matched by thresholds obtained from both static and moving gratings in a 4AFC task after the systematic shift in the CSF is considered, which in turn suggests that Curveball is a valid measure of contrast sensitivity. Notably, Curveball's CSFs appear to fall between the curves elicited by static and moving stimuli in conventional discrete psychophysics.

Figure 16:
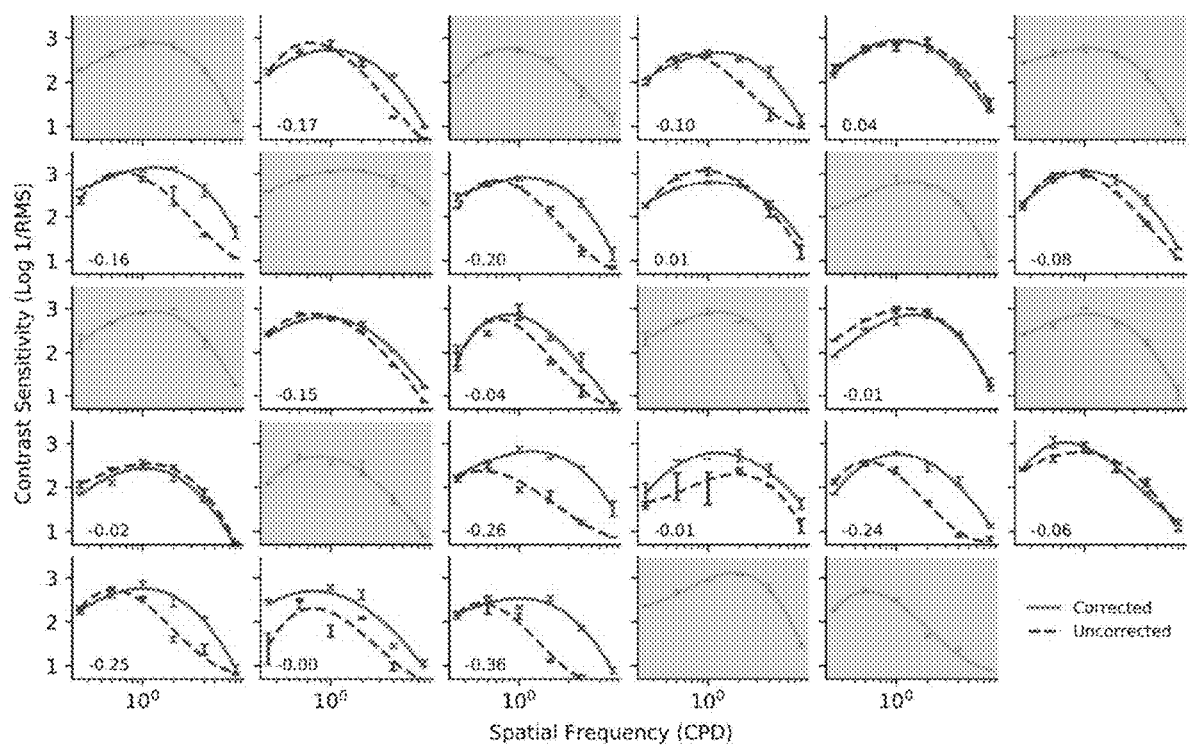
FIG. 16 depicts Curveball thresholds measured with and without visual correction. The layout and axes are identical to FIG. 12. The solid blue and dashed red lines represent Curveball CSFs obtained with and without corrective eyewear, respectively. The shear in the uncorrected CSF curve relative to the corrected curve is given in the bottom-left corner of each subplot. The standard Curveball thresholds for participants who did not complete the uncorrected condition have been left grayed out in this figure to permit easy comparison across figures. No other participants were excluded.

The CSFs produced by Curveball should be sensitive to the differences in visual acuity induced by refractive correction. Specifically, participants' contrast sensitivity should decrease more rapidly as a function of spatial frequency as their acuity worsens (i.e. when they remove their corrective lenses). If this is true, we would expect to find a relationship between the magnitude of the leftward shift in the CSF peak and the difference in eye chart acuity measured with and without visual correction. This relationship was examined for the eighteen participants with corrected-to-normal vision who performed an additional standard Curveball run without their corrective eyewear. The uncorrected Curveball CSFs for these participants are depicted together with their standard corrected Curveball CSFs in FIG. 16.

Figure 6:
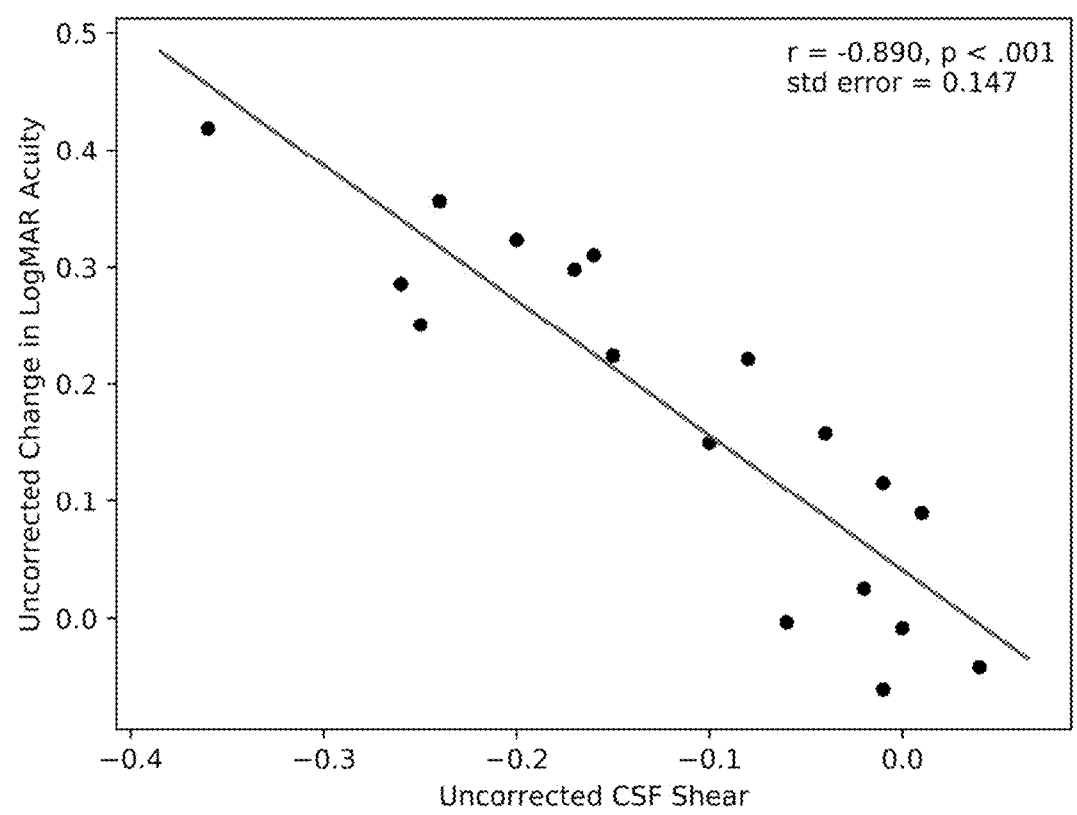
FIG. 6 depicts Regression plot of uncorrected change in LogMAR acuity against uncorrected CSF shear. Each point represents one of the eighteen participants who completed a Curveball run without their corrective eyewear. The change in acuity was significantly predicted by the shear of the uncorrected CSF relative to the corrected CSF in Curveball, in that larger shear values were associated with a greater loss of acuity (i.e. a more positive LogMAR value). The coefficient, p-value, and standard error of the correlation are depicted in the top-right corner and the gray line represents the line of best fit.

The effect of visual correction on the CSF was quantified with an affine transformation similar to that applied when comparing Curveball data to the 4AFC task, but in this case, separate transformations were optimized to account for the difference in corrected and uncorrected CSFs for each participant. The shear parameter of this transformation was then used as a measure of the change in the CSF curve: more negative shear indicates that the peak of the CSF shifted further to the left in the uncorrected condition relative to the corrected condition. A linear regression analysis revealed that uncorrected shear was highly and significantly predictive of the change in LogMAR acuity measured with the Tumbling 'E' chart, $r=-0.890$, $p<0.001$, in that more negative shear was associated with a larger loss of acuity from lack of corrective eyewear (as more positive LogMAR values represent worse vision). These data are shown with the line of best fit in FIG. 6. Interestingly, the line of best fit was approximately $y=-x$ (slope of $-1.153$ and intercept of 0.041). These results indicate that Curveball is highly sensitive to changes in visual acuity and refractive correction, which is expected of a useful measure of spatial visual function. It may be possible to estimate an individual's acuity from a single Curveball CSF, but this would require an empirical investigation of their absolute relationship.

Figure 17:
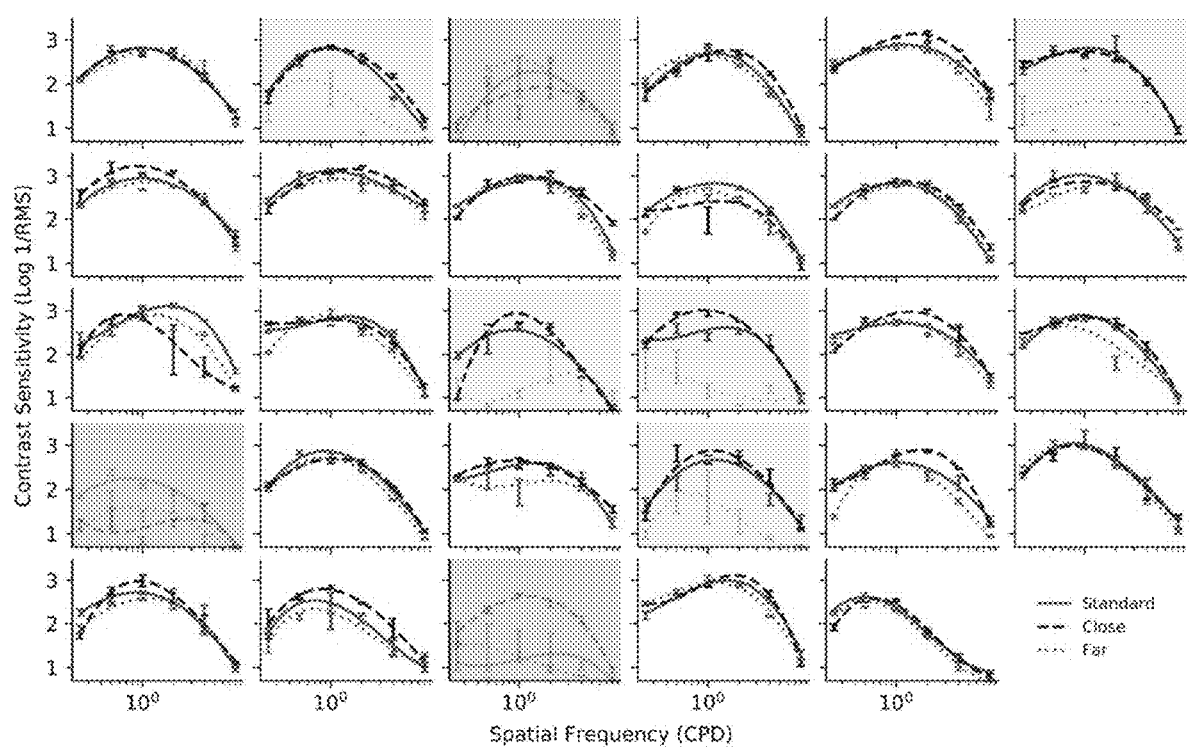
FIG. 17 depicts Curveball thresholds measured at different distances. The layout and axes are identical to FIG. 12, but correlations are not shown. The solid green, dashed blue, and dotted orange lines represent CSFs measured at standard (62 cm), close (47 cm), and far (77 cm) distances, respectively. Note that the spatial frequency units on the horizontal axis are only correct for the standard distance of 62 cm. The semi-grayed subplots indicate participants who were excluded from the far condition analysis due to an insufficient pursuit score in that condition; the fully-grayed subplots indicate participants who were excluded from both distance analyses due to insufficient pursuit scores in at least two of the three conditions.

If Curveball is to be a useful measure of vision in a range of clinical settings, it is helpful to have an understanding about how dependent the procedure is on participant distance. The task's reliance on distance was assessed by comparing the thresholds and pursuit scores measured from the standard (62 cm), 'close' (47 cm), and 'far' (77 cm) Curveball conditions in the second testing session (FIG. 17). The data suggest that deviations from the optimal eye tracker distance resulted in a greater number of 'dropped' trials for several participants. Pursuit ability fell below the exclusion threshold for two participants in the close condition and seven participants in the far condition. When these participants were excluded from the appropriate conditions, paired comparisons revealed that there was no significant difference in pursuit score between the standard and close conditions, $t(25)=-0.790$, $p=0.437$, but there was a significant decrease of 0.018 in pursuit score in the far condition relative to the standard condition, $t(21)=3.536$, $p=0.002$. This suggests that the increase in distance in the far condition added enough noise to their gaze data to push multiple participants' pursuit ability below the level required for the Curveball algorithm to accurately estimate sensitivity. Note that these findings apply specifically to the Tobii 4C eye tracker used in the experiment.

A repeated measures ANOVA revealed no change in mean sensitivity between the standard and close distance conditions, $F(1,26)=0.499$, $p=0.486$, but did reveal a significant interaction between distance and spatial frequency, $F(5,130)=3.036$, $p=0.013$. A linear trend contrast found that the difference between the standard and close conditions became significantly more positive as a function of increasing log spatial frequency, $t(26)=2.221$, $p=0.035$. This is expected: moving closer to the display increases the actual spatial frequency of each stimulus in degrees of visual angle and should shift the CSF to the right, as the presented stimuli are identical.

An analogous repeated measures ANOVA found a significant decrease of 0.135 log units of RMS sensitivity in the far condition relative to the standard condition, $F(1,20)=38.981$, $p<0.001$, but unlike in the close condition, there was no interaction between this distance change and spatial frequency, $F(5,100)=0.592$, $p=0.706$. The expected leftward shift in the CSF may have been masked by the increase in eye tracker noise at greater distances. Participants may have also found it more difficult to attend to the task in the far condition due to the screen's reduced presence in their field of view, which could explain the reduction in mean sensitivity.

Together, these results suggest that Curveball (when using the Tobii 4C) is more tolerant of decrements in user distance than increments relative to the optimal distance of 62 cm. This is likely a permanent limitation of display-mounted eye trackers, but its effect on the task may decrease as technology improves. For many participants, however, the task appears to remain reliable at a range of distances compatible with the display-mounted eye tracker.

Two participants were excluded from analysis of the 'dark' condition due to a tracking score below the exclusion threshold in that condition. A subsequent repeated measures ANOVA revealed that turning off the room lights had a small significant positive effect on mean sensitivity relative to the standard lights-on Curveball run conducted in the same testing session, $F(1,26)=4.670$, $p=0.040$, but no significant interaction between the change in illumination and spatial frequency, $F(5,130)=0.944$, $p=0.455$. These results suggest that a large change in room illumination (a decrease of 10 $cd/m^2$) has a minimal effect on Curveball performance. CSFs for the 'dark' condition are not depicted due to their high similarity to the curves from the standard conditions.

The findings provide strong evidence that Curveball is a reliable, accurate, and efficient objective measure of contrast sensitivity at working distance. Task repeatability was high, both within the same session (coefficient of repeatability 0.275) and across different days (coefficient of repeatability 0.227), and its consistency across changes in room illumination suggest that it is suitable for practical clinical settings. The procedure produces CSFs that are (a) systematically related to the CSFs obtained from both static and moving stimuli in a conventional staircase task and (b) highly predictive of the difference between corrected and uncorrected eye chart acuity. Curveball contrast sensitivity estimates are distorted in a predictable way as the user moves closer to the screen and the algorithm's ability to detect smooth tracking appears to degrade only gradually as distance from the eye tracker varies between the optimal and maximum distance allowed by the hardware. This suggests that the participant's distance can be continuously monitored using the eye tracker and used to compute the true spatial frequencies being measured in each trial when estimating the CSF. The display-mounted eye tracker used here required only half a second of one-point calibration at the start of the task for our smooth pursuit detection algorithm to perform well.

Critically, Curveball requires no volitional perceptual report and can potentially be administered with no instruction. Many participants reported that it was easier and more engaging than the conventional staircase task and indicated that they preferred the second Curveball-only testing session. Most importantly, the task is no less efficient than the best existing procedures based on perceptual report—even those that use Bayesian statistics and CSF curve parameterization—and is potentially more efficient due to its allowance of a flexible number of repeats per threshold. A single threshold estimate for one spatial frequency takes less than ten seconds to obtain, and the precision of that estimate rapidly improves as additional repeats are conducted and dropped trials discarded. These dropped trials are likely to cause the trial to end much earlier than it otherwise would, and future implementations of Curveball could potentially detect these false negatives and respond by adapting the number of repeats needed for that spatial frequency in real time. For example, participants who exhibit a sufficiently low difference between the first two repeats of a given threshold, in addition to a sufficiently high pursuit score, could skip the third and fourth repeats at that spatial frequency.

Another advantage of Curveball (and gaze-based tasks in general) is the ability to extract other information about the participant's visual function from the eye tracking data collected during the procedure. This could make the task even more useful for testing participants with brain injury or other cognitive impairments, as these individuals are likely to exhibit low-level ocular or cortical dysfunction that can be measured from Curveball even if accurate contrast thresholds cannot be obtained. The ability to smoothly pursue a target, for example, is a useful dimension of visual function that Curveball already exploits to determine stimulus visibility. Curveball data could be further leveraged to determine how pursuits and saccades depend on stimulus orientation, movement direction, and location in the visual field, all of which naturally vary as the target moves around the display. Catch-up saccade latency could be inferred from the participant's response when the target appears at the start of a new trial or abruptly rebounds off the edge of the display. Specific dysfunctions, such as pathological nystagmus, could also be detected and quantified from the gaze data. It may even be possible to quantify aspects of attention based on high-level responses (e.g. patterns of visual search across the display).

A system according to the present invention may include a display; an eye-tracking device configured to detect the gaze position of one or both eyes; and a pursuit detector executed by at least one processor. The pursuit detector may be configured to (1) display one or more variable-contrast stimuli, each of which moves from a first location on the display to a second location on the display; (2) receive, from the eye-tracking device, the gaze position signal detected from one or both eyes as each variable-contrast stimulus moves from the first location to the second location; (3) calculate a set of trajectory-match scores by comparing the gaze position signal to the position of each stimulus over a time window; (4) identify, based upon the set of trajectory-match scores, the visual function of a subject; and (5) display additional audiovisual stimuli coincident with or between the movements of the variable-contrast stimuli to facilitate attention, provide a break to the participant, or provide feedback on performance.

The pursuit detector may further be configured to produce real-time, frame-by-frame inferences about stimulus visibility based on the similarity between gaze and stimulus trajectories, to determine a trajectory-match score for each stimulus on every frame by, for example, (1) identifying and discarding samples of gaze position that are not consistent with the known limitations of the human eye and/or human visual system; (2) computing a stimulus trajectory function from each variable-contrast stimulus position signal on each frame as that stimulus moves from the first location to the second location; (3) constructing an expected gaze trajectory function for each stimulus trajectory function based on the most recent value of the gaze position signal on each frame;

(4) computing an actual gaze trajectory function on each frame from the gaze position signal over the same time window as the stimulus trajectory function; and (5) calculating a trajectory-match score for each variable-contrast stimulus based on the quantitative spatiotemporal agreement between that stimulus's expected gaze trajectory function and the participant's actual gaze trajectory function on each frame. Sixty trajectory-match scores may be produced per stimulus per second.

A method in accordance with the present invention may include the steps of (1) displaying, on a computer screen, one or more variable-contrast stimuli that each move from a first location to a second location; (2) generating, by an eye-tracking monitor, a gaze position signal as each visual stimulus moves from its first location to its second location, the gaze position signal detecting a position of one or both eyes; (3) filtering the gaze position signal by discarding samples that are not consistent with known limitations of the human eye and/or human visual system; (4) calculating a trajectory-match score from comparison of the gaze position signal and stimulus position over a time window; (5) identifying the visual function of the subject based upon the trajectory-match score; and (6) displaying additional audio-visual stimuli during or between the movements of the variable-contrast stimuli to facilitate attention, provide breaks, or provide performance feedback. The variable-contrast stimulus may increase in contrast or decrease in contrast. The stimulus contrast change may be perceptually continuous. The variable-contrast stimulus may change in a step-wise manner by multiplying the current contrast by a variable between 0.5-1.5 on each frame.

In an alternative embodiment, a plurality of Curveball stimuli may be depicted and move smoothly in a pattern on the display, rather than stimuli randomly drifting around the display one at a time. For example, a predetermined number of Curveball stimuli (e.g., six stimuli) may move smoothly in a circle in the center of the display or may follow a path through an invisible grid or other geometry. When the observer begins to track one of the stimuli, a number of the other stimuli may temporarily disappear to disrupt global motion cues that could allow the observer to continue tracking a (perceptually) featureless local region. For example, if six Curveball stimuli are depicted as moving smoothly in a circle in the center of the display, the four stimuli closest to the stimuli that the observe begins to track (i.e. all but the stimulus directly opposite the tracked stimulus) may temporarily disappear. The stimuli may reappear when the observer stops tracking. The ongoing presence of the opposite stimulus ensures that the observer is always provided with a new stimulus to track upon losing the first; the observer may return to a stimulus later if they have not yet pursued it to threshold.

In this embodiment, rather than continuously fading, tracked stimuli may change in both contrast and spatial frequency simultaneously after each discrete burst of tracking. The progression of each stimulus may follow a sequence of combinations of spatial frequency and contrast (a "sweep") through the 2D CSF space, rather than varying only contrast (i.e. a vertical vector) or only spatial frequency (i.e. a horizontal vector). The variation of both contrast and spatial frequency may ensure that the stimulus continually refreshes its appearance, which counteracts the tiresome nature of extended tracking.

These sweep sequences may take the form of line segments or vectors through the CSF space that may share a common origin, which may be chosen empirically to be maximally visible to the widest range of observers with different visual ability (e.g. high contrast and low-medium spatial frequency). These vectors may "puncture" various points along the observer's CSF curve at a more perpendicular angle than conventional horizontal or vertical sweeps, which reduces any negative effects of measurement error on curve estimation.

Progress along each sweep sequence may "spill over" into progress along nearby sweep sequences (e.g. adjacent sweep vectors following similar angles away from the origin), which is an optimization made possible by conservative, empirically-justified assumptions about the continuity and curvature of the CSF. Sweep sequences that have been indirectly progressed this way may start further along their sequence (e.g. away from the shared vector origin) than they normally would, which removes redundant trials from the task and saves time. The subset of sweep sequences ("basis sweeps") whose threshold is the most empirically informative about the overall CSF and sensitivity to disease may be identified through testing and may be tested first, to ensure that information is collected in the most efficient manner given the limited time of many hospitalized participants. The single most informative sweep vector is referred to herein as the Concuity sweep. Also, eye movement kinematics generated as part of the evidence-of-visibility score computations, such as tracking accuracy, direction, duration, and saccade interspersion, may be collected and analyzed as metrics of visuomotor function.

Figure 7:
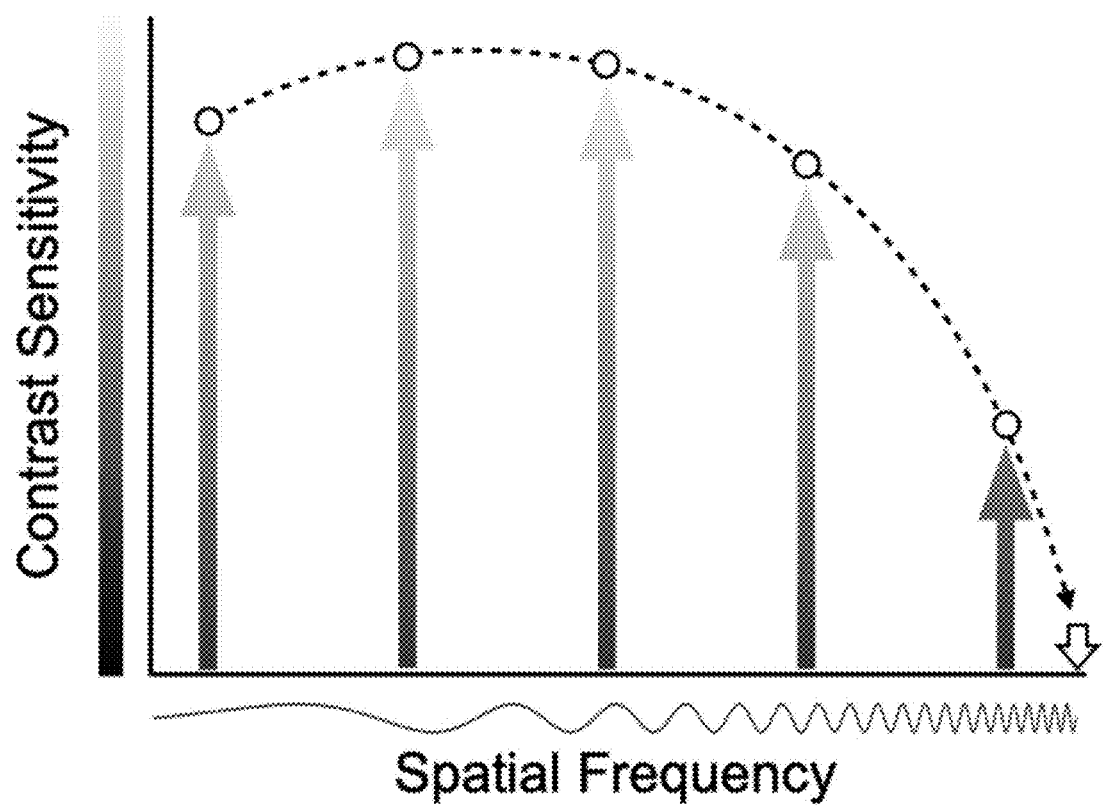
FIG. 7 is a graph showing an assessment of acuity and generation of a contrast sensitivity function (CSF).

As shown in FIG. 7, spatial vision can be specified as a 2D stimulus visibility space, with spatial frequency varying on the X-axis (sinusoidally-undulating line), and contrast varying on the Y-axis (vertical rectangle with changing contrast relative to the white background). Acuity may be defined as the highest spatial frequency that is visible at maximal stimulus contrast (e.g. open arrow). A contrast sensitivity function (CSF), shown as a dotted line, may be estimated from the measurement of minimal contrast visibility over a range of spatial frequencies (vertical arrows and open circles). The CSF intersects with the X-axis (closed arrow) at acuity. The Curveball approach to measuring a CSF proceeds through multiple stimulus variations much faster than approaches that use discrete trials, and spends less time (trials) near the limit of ability, which reduces the fatigue of testing.

Figure 8:
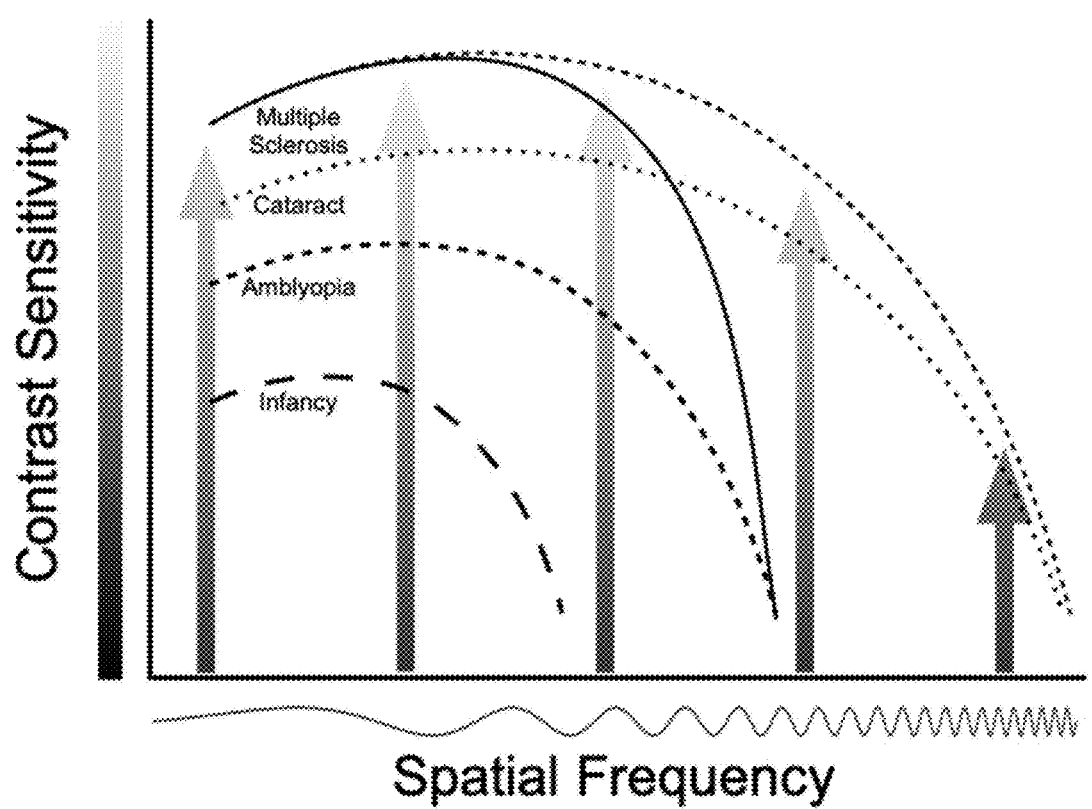
FIG. 8 is a graph depicting the limits of measuring acuity and CSFs.

Referring to FIG. 8, acuity may be used as a simple and fast measure of spatial visual health and disease, but it has limited sensitivity to detect small, but meaningful variation in brain-related visual function. Measures of contrast sensitivity are often superior to acuity in detecting spatial visual abnormalities, but the time and expertise required to generate CSFs is substantial, and thus, contrast measures are not generally used for such diagnostic purposes. Moreover, no typical single measure of contrast sensitivity (e.g., one of the vertical arrows) would satisfactorily define the interaction between spatial frequency and contrast, nor capture the type of variation that typically distinguishes visual disorders and age-related change in visual function (illustrated with idealized overlaid example CSFs). Using idealized sample data, FIG. 8 depicts how conventional testing trajectories that are strictly vertical or horizontal may entirely fail to intersect the CSF at any point.

Figure 9:
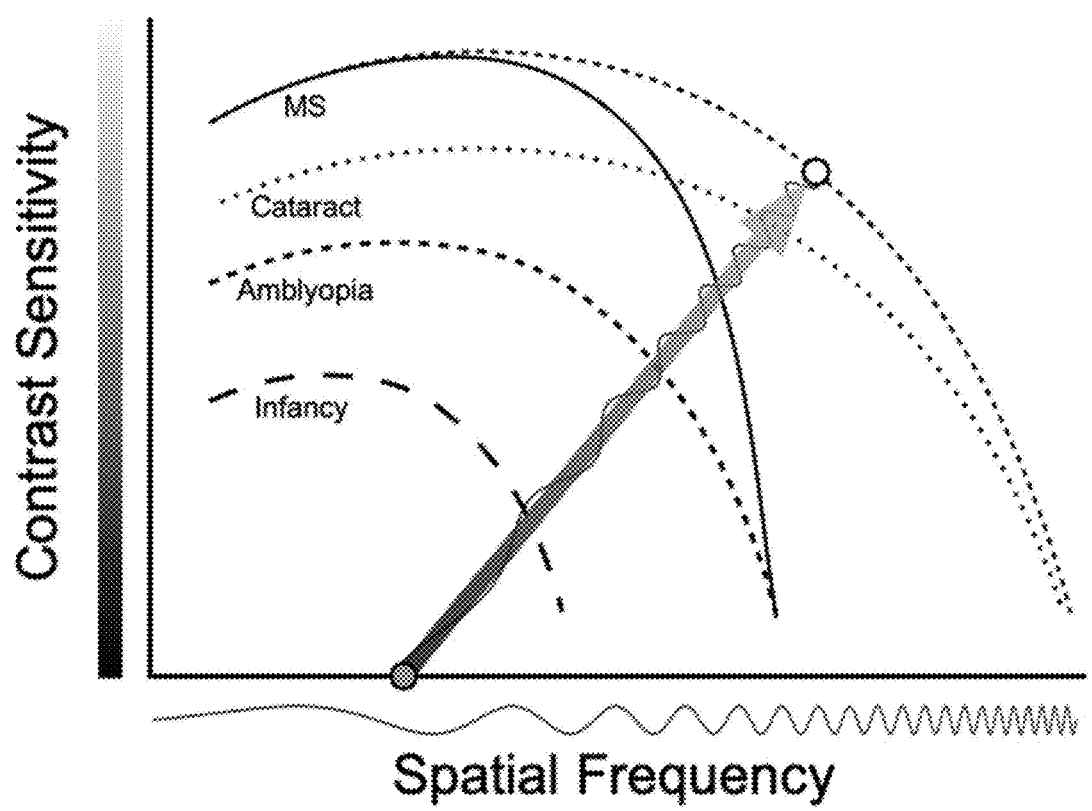
FIG. 9 is a graph depicting a sweep vector approach to obtaining a single measure of spatial visual function.

Unlike defining a single point on the CSF through the manipulation of contrast only, or through measuring visual acuity, as is typically done, as shown in FIG. 9, the most informative single point on the CSF (open circle on outer dashed line) may be measured by simultaneously varying contrast and spatial frequency during a single gaze-driven sweep through the 2D stimulus visibility space (angled arrow with gradated luminance and spatial frequency variation) using the present invention's algorithm. This approach holds promise to identify a visual deficit that single measures of contrast sensitivity would miss. The vector would intersect with CSFs that vary widely in their shape as a function of disease and age. The optimal position of the sweep's origin (gray-filled circle on the X-axis), as well as the angle of the vector that defines the optimal proportion of spatial frequency variation to contrast variation, may be estimated and refined empirically through the statistical analysis of a large database of CSFs.

Figure 10:
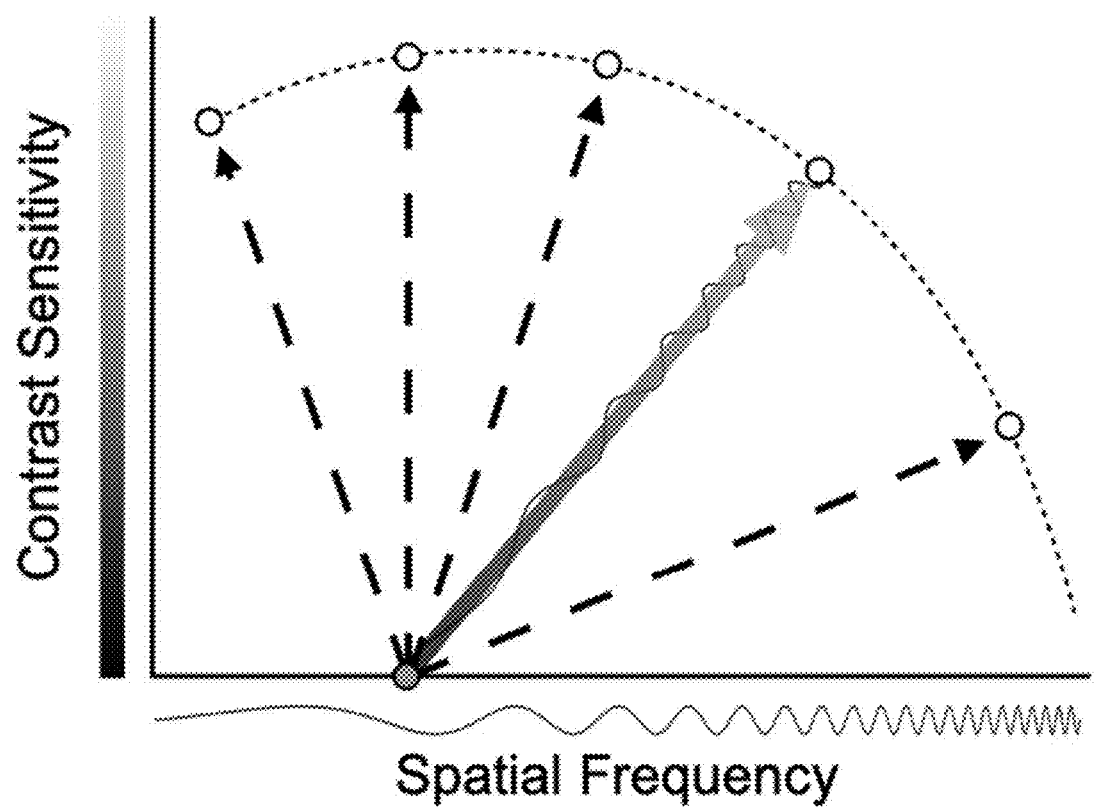
FIG. 10 is a graph depicting a "sweep trajectory" approach to measuring the Concuity point on the CSF.

Referring to FIG. 10, the "sweep" approach to measuring the Concuity point on the CSF can be generalized to the measurement of the rest of the CSF. The simultaneous manipulation of contrast and spatial frequency (dotted lines with arrows) is an efficient way to generate the points that define a CSF (open circles) because (a) the stimulus at the origin is common to all vectors, and is optimally visible to the widest range of viewers, and (b) the simultaneous manipulation of contrast (a continuous variable) and spatial frequency (a discrete variable) makes the stimulus more interesting and more easily tracked compared to stimuli that vary in contrast alone. In other applications, sweep sequences other than vectors may be useful. For example, sweep sequences that "skate" along an existing estimate of a participant's CSF could be used to make detailed refinements to that CSF.

Referring to FIGS. 11A and 11B, the "sweep vector" approach to measuring CSFs also enables a way to predict the visibility of stimuli on adjacent vectors, which can be used to improve the efficiency of the task. The visibility of stimuli on sweep vectors adjacent to (i.e. a small angular difference away from) the sweep vector currently being measured can be predicted with high confidence, because (a) human CSFs generally approximate a continuous arc regardless of disease and age, (b) the sweep vectors used to measure a CSF emanate from the same origin, and (c) each vector intersects the CSF at an approximately perpendicular angle. The graphs of a Curveball CSF experiment in progress (FIG. 11A) and at completion (FIG. 11B) show how the procedure works. Each straight line of dots represents a single sweep vector. Each dot in the sequence represents a single stimulus that was successfully tracked, causing the next stimulus in the sweep to appear. The final dot in each sequence was not successfully tracked, which terminates the sweep and defines one point of the CSF. As progress is directly made along the tested vector via successful tracking, indirect progress is also made (but to a lesser degree) along adjacent vectors (shorter lines on either side) even though they will not be directly tested until later. Thus, when each of those adjacent sweep vectors are subsequently tested, the initial stimulus conditions do not have to be those at the origin (central dot), but instead can begin at the limit of inferred indirect progress already made within that sweep (final dots on the short vectors). This is because there is a high probability that the participant can easily see the stimulus, even though the specific stimulus conditions were never tested. This process of generalizing the visibility of stimuli from one sweep vector to another reduces the time required to measure a CSF because highly visible stimuli do not need to be repeatedly assessed. The exact degree to which progress along one vector can be inferred from progress on another (for example, inference weight as a function of relative sweep angle and relative sweep progress) may be empirically determined by sampling the natural range of CSFs within specific populations.

A system in accordance with the present invention may include a display, an eye-tracking device configured to detect the gaze position of one or both eyes of the person, a non-transitory memory having a machine-readable medium comprising machine executable code; and one or more processors coupled to the memory, said one or more processors configured to execute the machine executable code. Execution of the machine executable code may cause the one or more processors to (1) generate an ordered sequence of a set of one or more visual stimuli; (2) present at a first area of the display a first visual image; (3) receive from the eye-tracking device data indicating a second area of the display to which the person's gaze is directed; (4) pre-calibrate the eye-tracking device based on the location of the first area and the location of the second area; (5) store in the non-transitory memory a software algorithm that sets a path for each of the visual stimuli to follow on the display; (6) present on the display a first visual stimulus of the set of one or more visual stimuli, wherein the first visual stimulus moves in a path on the display as set by the software algorithm for a first period of time; (7) receive from the eye-tracking device data indicating a gaze position and an eye position of one or both eyes of the person for the first period of time; (8) calculate an evidence-of-visibility score by comparing the gaze position and eye position of one or both eyes of the person during the first period of time to the position on the display of the first visual stimulus during the first period of time; (9) modify, based upon the evidence-of-visibility score, the contrast or spatial frequency of the first visual stimulus; (10) calibrate the eye-tracking device based on the data indicating a gaze position and an eye position of one or both eyes of the person and the position of first visual stimulus over the first period of time; and (11) determine, based upon the evidence-of-visibility score, a visual function of the person.

Calculating the evidence-of-visibility score may produce real-time, frame-by-frame inferences about stimulus visibility based on the relationship between gaze and stimulus trajectories, to determine an evidence-of-visibility score for each stimulus on every frame. The method of calculating the evidence-of-visibility score may include (1) identifying and discarding samples of gaze position that are not consistent with the known limitations of the human eye and/or human visual system; (2) identifying and discarding samples of gaze position that are malformed by blinks, failure to attend to the display, and/or invalid person position relative to the display; (3) identifying fixation events by analyzing the 2D dispersion metric of gaze position and comparing gaze position to the positions of all presented stimuli; (4) identifying saccade events by detecting high-velocity, high-acceleration, near-linear eye movements and comparing the endpoint of the saccade to the positions of all presented stimuli; (5) identifying smooth pursuit events by detecting mid-velocity, low-acceleration eye movements; and/or (6) identifying optokinetic nystagmus events by detecting smooth pursuit events interspersed with saccade events occurring in near-opposing directions.

Additionally, the method of calculating the evidence-of-visibility score may comprise: (a) computing a stimulus trajectory function from each variable-spatial-frequency variable-contrast stimulus position signal on each frame as that stimulus moves from the first location to the second location; (b) constructing an expected gaze trajectory function for each stimulus trajectory function based on the most recent value of the gaze position signal on each frame; (c) computing an actual gaze trajectory function on each frame from the gaze position signal over the same time window as the stimulus trajectory function; (d) identifying target-tracking events for each presented stimulus based on the quantitative spatiotemporal agreement between that stimulus's expected gaze trajectory function and the person's actual gaze trajectory function on each frame; (e) calculating and applying both automated time decay penalties and added penalties from the absence of target-correlated gaze events; (f) computing evidence weights for each type of gaze event using the geometric statistics of the paths and appearance of the presented stimuli; and (g) computing an evidence-of-visibility score for each presented stimulus by calculating a weighted sum of evidence from all computed gaze events and penalties. Between 30-120 evidence-of-visibility scores may be produced per presented stimulus per second, depending on the refresh rate of the display.

While the invention has been described in detail with reference to embodiments for the purposes of making a complete disclosure of the invention, such embodiments are merely exemplary and are not intended to be limiting or represent an exhaustive enumeration of all aspects of the invention. It will be apparent to those of ordinary skill in the art that numerous changes may be made in such details, and the invention is capable of being embodied in other forms, without departing from the spirit, essential characteristics, and principles of the invention. Also, the benefits, advantages, solutions to problems, and any elements that may allow or facilitate any benefit, advantage, or solution are not to be construed as critical, required, or essential to the invention. The scope of the invention is to be limited only by the appended claims.

What is claimed is:

1. A system for assessing a visual function of a person, comprising:
   a display;
   an eye-tracking device configured to detect the gaze position of one or both eyes of the person;
   a non-transitory memory having a machine-readable medium comprising machine executable code; and
   one or more processors coupled to the non-transitory memory, said one or more processors configured to execute the machine executable code, causing the one or more processors to:
   a) generate an ordered sequence of a set of one or more visual stimuli;
   b) present at a first area of the display a first visual image;
   c) receive from the eye-tracking device data indicating a second area of the display to which the person's gaze is directed;
   d) pre-calibrate the eye-tracking device based on the location of the first area and the location of the second area;
   e) store in the non-transitory memory a software algorithm that sets a path for each of the visual stimuli of the set to follow on the display;
   f) store in the non-transitory memory an evidence-of-visibility score and one or more predetermined modification values;
   g) present on the display a first visual stimulus of the set of one or more visual stimuli, wherein the first visual stimulus moves in a path on the display as set by the software algorithm for a first period of time;
   h) receive from the eye-tracking device first data indicating a gaze position and an eye position of one or both eyes of the person for the first period of time;
   i) use the first data to determine whether the gaze position and eye position of one or both eyes of the person during the first period of time are directed to the position on the display of the first visual stimulus during the first period of time;
   j) select a predetermined modification value based on whether the gaze position and eye position of one or both eyes of the person during the first period of time are directed to the position on the display of the first visual stimulus during the first period of time;
   k) increase or decrease the evidence-of-visibility score by the predetermined modification value;
   l) decreasing, when the evidence-of-visibility score resulting in k) is above a predetermined threshold value indicating that the person can see the first visual stimulus, the contrast and/or changing the spatial frequency of the first visual stimulus;
   m) reiterating steps g) through l) for each stimulus of the set, except when in step l) the evidence-of-visibility resulting from k) is below a predetermined threshold value, thus indicating that the person can no longer see the visual stimulus, thus identifying the contrast and/or spatial frequency limit of the visual stimulus so as to determine a visual function of the person.

2. The system of claim 1, wherein the machine executable code is further capable of causing the one or more processors to:
   after determining that an evidence-of-visibility score is below a predetermined threshold,
   further present at a second area of the display, at a different location that the first visual stimulus, a second visual image.

3. The system of claim 1, wherein the first visual stimulus is a sine grating signal.

4. The system of claim 1, wherein the first visual stimulus is an isotropic filtered texture.

5. The system of claim 1, wherein the first visual stimulus is an anisotropic filtered texture.

6. The system of claim 1, wherein the person's gaze is pre-calibrated using a one-point calibration procedure.

7. The system of claim 1, wherein the person's gaze is pre-calibrated using a four-point calibration procedure.

8. The system of claim 1, wherein the visual function is the person's contrast sensitivity function and in step l), the contrast is decreased.

9. The system of claim 1, wherein the one or more processors coupled to the memory configured to execute the machine executable code causing the one or more processors to further calibrate the eye-tracking device based on the first data indicating a gaze position and an eye position of one or both eyes of the person and the position of first visual stimulus over the first period of time.

10. A method for assessing a visual function of a person, comprising:
    i) generating one or more sequences of one or more visual stimuli;
    ii) pre-calibrating an eye-tracking device based on the person's gaze;
    iii) determining, using an algorithm, a path for each of the visual stimuli to follow on a display;
    iv) presenting on the display during a first period of time a first visual stimulus of a first of the one or more sequences of visual stimuli, wherein the first visual stimulus moves on the display along a first path determined by the algorithm for the first visual stimulus;
    v) receiving, from an eye-tracking device, one or more gaze position signals and one or more eye position signals detected from one or both eyes of the person as the first visual stimulus moves along the first path on the display;
vi) calculating a first evidence-of-visibility score for the first visual stimulus by comparing the one or more gaze position signals and one or more eye position signals to one or more locations of the first visual stimulus on the display during the first period of time;
vii) modifying, based upon the first evidence-of-visibility score, the appearance contrast and/or the spatial frequency of the first visual stimulus;
viii) calibrating the eye-tracking device based on the evidence-of-visibility score;
ix) reiterating steps iv) through vii) until the evidence of visibility score calculated in vi) falls below a predetermined threshold value, thus indicating that the subject can no longer see the first visual stimulus, thereby determining the visual function of the person.

11. The method of claim 10, wherein modifying, based upon the first evidence-of-visibility score, the appearance of the first visual stimulus comprises increasing the contrast of the first visual stimulus.

12. The method of claim 10, wherein modifying, based upon the first evidence-of-visibility score, the appearance of the first visual stimulus comprises decreasing the contrast of the first visual stimulus.

13. The method of claim 10, wherein modifying, based upon the first evidence-of-visibility score, the appearance of the first visual stimulus comprises modifying the contrast of the first visual stimulus, wherein the modification is imperceptible to the person.

14. The method of claim 10, wherein modifying, based upon the first evidence-of-visibility score, the appearance of the first visual stimulus comprises increasing the spatial frequency components of the first visual stimulus.

15. The method of claim 10, wherein modifying, based upon the first evidence-of-visibility score, the appearance of the first visual stimulus comprises decreasing the spatial frequency components of the first visual stimulus.

16. The method of claim 10, wherein the appearance of the first visual stimulus changes in a step-wise manner by multiplying the contrast of the first visual stimulus by a variable between 0.5-1.5 on each frame presented on the display.

17. The method of claim 10, wherein the appearance of the first visual stimulus changes in a step-wise manner by multiplying the spatial frequency components of the first visual stimulus by a variable between 0.5-1.5 on each frame presented on the display.

18. The method of claim 10, wherein the visual function is the person's contrast sensitivity function.

19. The method of claim 18, wherein each visual stimulus is parameterized by a spatial frequency value and a contrast value.

20. The method of claim 19, wherein one or more of the visual stimuli are depicted as sine wave gratings.

21. The method of claim 19, wherein one or more of the visual stimuli are depicted as band-filtered isotropic textures.

22. The method of claim 19, wherein one or more of the visual stimuli are depicted as band-filtered anisotropic textures.

23. The method of claim 19, wherein a sequence of spatial frequency and contrast configurations of an ordered sequence of visual stimuli comprise a continuous trajectory through the contrast sensitivity function space.

24. The method of claim 10, further comprising:
if the evidence-of-visibility score of the first visual stimulus is outside a first predetermined range of values, terminating display of the first visual stimulus;
and presenting on the display a second visual stimulus of the first of the one or more sequences of visual stimuli, wherein the second visual stimulus moves according to a second path determined by the algorithm for the second visual stimulus.

25. The method of claim 24, wherein the evidence-of-visibility score for the first visual stimulus is used to determine the appearance of the second visual stimulus before the second visual stimulus has been presented.

26. The method of claim 10, further comprising:
if the evidence-of-visibility score of a visual stimulus of the first of the one or more sequences of visual stimuli is outside a second predetermined range of values, terminating display of that visual stimulus; and presenting on the display the first visual stimulus of a second of the one or more sequences of visual stimuli, wherein that first visual stimulus moves according to a second path determined by the algorithm for that first visual stimulus.

27. The method of claim 26, wherein the evidence-of-visibility scores for one or more visual stimuli in the first of the one or more sequences of visual stimuli are used to determine the appearance of one or more visual stimuli in the second of the one or more sequences of visual stimuli before the visual stimuli in the second of the one or more sequences have been presented.

* * * * *